(12) United States Patent
Kusters et al.

(10) Patent No.: US 12,343,738 B2
(45) Date of Patent: Jul. 1, 2025

(54) CONTINUOUS FLOW CENTRIFUGATION CHAMBERS

(71) Applicant: Fenwal, Inc., Lake Zurich, IL (US)

(72) Inventors: Benjamin E. Kusters, Pleasant Prairie, WI (US); Richard I. Brown, Northbrook, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 548 days.

(21) Appl. No.: 17/712,531

(22) Filed: Apr. 4, 2022

(65) Prior Publication Data

US 2022/0314237 A1 Oct. 6, 2022

Related U.S. Application Data

(60) Provisional application No. 63/296,532, filed on Jan. 5, 2022, provisional application No. 63/211,652, filed
(Continued)

(51) Int. Cl.
*B04B 5/04* (2006.01)
*B04B 11/02* (2006.01)

(52) U.S. Cl.
CPC ............ *B04B 5/0442* (2013.01); *B04B 11/02* (2013.01)

(58) Field of Classification Search
None
See application file for complete search history.

(56) References Cited

U.S. PATENT DOCUMENTS

| 4,010,894 A | 3/1977 | Kellogg et al. |
| 4,120,449 A | 10/1978 | Brown et al. |

(Continued)

FOREIGN PATENT DOCUMENTS

| EP | 1949923 A2 | 7/2008 |
| WO | WO 96/33023 A1 | 10/1996 |

(Continued)

OTHER PUBLICATIONS

European Patent Office, "Extended European Search Report", issued in connection with application No. 22166498.0 on Oct. 27, 2022, 11 pages.
(Continued)

*Primary Examiner* — Peter Keyworth
(74) *Attorney, Agent, or Firm* — Cook Alex Ltd.

(57) ABSTRACT

Fluid separation chambers are provided with a central hub, with generally annular low- and high-G walls extending about the hub to define therebetween a separation channel. A plurality of radial walls extend from the hub to the channel to define an inlet passage and two outlet passages. The low-G wall may include an air drain taper and/or a decreased radius adjacent to an associated outlet passage. The radius of the low-G wall and (optionally) the high-G wall may gradually decrease from an upstream end of the channel to a downstream end for improved separation. A ramp may extend across the channel, with a bottom end positioned adjacent to the bottom end of the channel, where the outlet passages open into the channel. The outlet passage associated with the high-G wall may open into the channel at an upstream end of the ramp or at the upstream end of the channel.

20 Claims, 18 Drawing Sheets

Related U.S. Application Data on Jun. 17, 2021, provisional application No. 63/170,678, filed on Apr. 5, 2021.

(56) References Cited

U.S. PATENT DOCUMENTS

| | | | |
|---|---|---|---|
| 4,386,730 A | 6/1983 | Mulzelt | |
| 4,387,848 A | 6/1983 | Kellogg et al. | |
| 4,419,089 A | 12/1983 | Kolobow et al. | |
| 4,647,279 A | 3/1987 | Mulzet et al. | |
| 4,708,712 A | 11/1987 | Mulzet | |
| 4,851,126 A | 7/1989 | Schoendorfer | |
| 4,934,995 A | 6/1990 | Cullis | |
| 5,217,426 A | 6/1993 | Bacehowski et al. | |
| 5,370,802 A | 12/1994 | Brown | |
| 5,649,903 A | 7/1997 | Deniega et al. | |
| 5,674,173 A | 10/1997 | Hlavinka et al. | |
| 5,722,926 A | 3/1998 | Hlavinka et al. | |
| 5,868,696 A | 2/1999 | Giesler et al. | |
| 5,906,570 A | 5/1999 | Langley et al. | |
| 5,913,768 A | 6/1999 | Langley et al. | |
| 5,939,319 A | 8/1999 | Hlavinka et al. | |
| 5,951,877 A | 9/1999 | Langley et al. | |
| 5,993,370 A | 11/1999 | Brown et al. | |
| 5,996,634 A | 12/1999 | Dennehey et al. | |
| 6,022,306 A | 2/2000 | Dumont et al. | |
| 6,051,146 A | 4/2000 | Green et al. | |
| 6,053,856 A | 4/2000 | Hlavinka | |
| 6,071,422 A | 6/2000 | Hlavinka et al. | |
| 6,277,060 B1 | 8/2001 | Neumann | |
| 6,334,842 B1 | 1/2002 | Hlavinka et al. | |
| 6,348,156 B1 | 2/2002 | Vishnoi et al. | |
| 6,582,349 B1 | 6/2003 | Cantu et al. | |
| 6,849,039 B2 | 2/2005 | Min et al. | |
| 6,875,191 B2 | 5/2005 | Smith et al. | |
| 7,011,761 B2 | 3/2006 | Muller | |
| 7,087,177 B2 | 8/2006 | Min et al. | |
| 7,297,272 B2 | 11/2007 | Min et al. | |
| 7,354,415 B2 | 4/2008 | Bainbridge et al. | |
| 7,438,679 B2 | 10/2008 | Hlavinka et al. | |
| 7,442,178 B2 | 10/2008 | Chammas | |
| 7,452,322 B2 | 11/2008 | Headley et al. | |
| 7,470,371 B2 | 12/2008 | Dorian et al. | |
| 7,473,216 B2 | 1/2009 | Lolachi et al. | |
| 7,497,944 B2 | 3/2009 | Hogberg et al. | |
| 7,549,956 B2 | 6/2009 | Hlavinka et al. | |
| 7,582,049 B2 | 9/2009 | Hlavinka et al. | |
| 7,588,692 B2 | 9/2009 | Antwiler et al. | |
| 7,601,268 B2 | 10/2009 | Ragusa | |
| 7,648,452 B2 | 1/2010 | Holmes et al. | |
| 7,648,639 B2 | 1/2010 | Holmes et al. | |
| 7,674,221 B2 | 3/2010 | Hudock et al. | |
| 7,708,152 B2 | 5/2010 | Dorian et al. | |
| 7,708,710 B2 | 5/2010 | Min et al. | |
| 7,766,809 B2 | 8/2010 | Dolecek et al. | |
| 7,811,463 B2 | 10/2010 | Dolecek et al. | |
| 7,819,793 B2 | 10/2010 | Lindell et al. | |
| 7,824,559 B2 | 11/2010 | Dorian et al. | |
| 7,833,185 B2 | 11/2010 | Felt et al. | |
| 7,837,884 B2 | 11/2010 | Dorian et al. | |
| 7,857,744 B2 | 12/2010 | Langley et al. | |
| 7,866,485 B2 | 1/2011 | Dorian et al. | |
| 7,867,159 B2 | 1/2011 | Dolecek et al. | |
| 7,934,603 B2 | 5/2011 | Eaton et al. | |
| 7,943,916 B2 | 5/2011 | Carter et al. | |
| 7,963,901 B2 | 6/2011 | Langley et al. | |
| 7,976,796 B1 | 7/2011 | Smith et al. | |
| 7,981,019 B2 | 7/2011 | Holmes et al. | |
| 7,987,995 B2 | 8/2011 | Dorian et al. | |
| 8,012,077 B2 | 9/2011 | Hoeppner | |
| 8,057,377 B2 | 11/2011 | Holmes et al. | |
| 8,075,468 B2 | 12/2011 | Min et al. | |
| 9,327,296 B2 | 5/2016 | Pieper et al. | |
| 2002/0179544 A1 | 12/2002 | Johnson et al. | |
| 2003/0066807 A1 | 4/2003 | Suzuki | |
| 2003/0166445 A1 | 9/2003 | Rochat | |
| 2003/0173274 A1 | 9/2003 | Corbin, III et al. | |
| 2003/0211927 A1* | 11/2003 | Cantu | A61M 1/362266 494/3 |
| 2004/0065626 A1 | 4/2004 | Woo | |
| 2004/0245189 A1 | 12/2004 | Robinson et al. | |
| 2008/0147240 A1 | 6/2008 | Hudock et al. | |
| 2008/0149564 A1 | 6/2008 | Holmes | |
| 2008/0153686 A1 | 6/2008 | Rochat | |
| 2008/0171646 A1 | 7/2008 | Dolecek et al. | |
| 2008/0248938 A1 | 10/2008 | Chammas | |
| 2008/0283473 A1 | 11/2008 | Holmes et al. | |
| 2009/0259162 A1 | 10/2009 | Ohashi et al. | |
| 2009/0272701 A1 | 11/2009 | Holmes et al. | |
| 2009/0286221 A1 | 11/2009 | Klip et al. | |
| 2009/0298665 A1 | 12/2009 | Dolecek et al. | |
| 2009/0317305 A1 | 12/2009 | Hudock et al. | |
| 2010/0026986 A1 | 2/2010 | Stanton et al. | |
| 2010/0042037 A1 | 2/2010 | Felt et al. | |
| 2010/0081196 A1 | 4/2010 | Felt et al. | |
| 2010/0210441 A1 | 8/2010 | Dolecek | |
| 2010/0267538 A1 | 10/2010 | Green et al. | |
| 2010/0273627 A1 | 10/2010 | Hudock et al. | |
| 2011/0003675 A1 | 1/2011 | Dolecek | |
| 2011/0028295 A1 | 2/2011 | Menhennett et al. | |
| 2011/0059834 A1 | 3/2011 | Eberle | |
| 2011/0077140 A1 | 3/2011 | Holmes et al. | |
| 2011/0086752 A1 | 4/2011 | Brierton | |
| 2011/0100919 A1 | 5/2011 | Dorian et al. | |
| 2011/0136646 A1 | 6/2011 | Pearce et al. | |
| 2011/0136650 A1 | 6/2011 | Ellingboe et al. | |
| 2011/0152055 A1 | 6/2011 | Pittinger et al. | |
| 2011/0178453 A1 | 7/2011 | Pages et al. | |
| 2011/0224064 A1 | 9/2011 | Pittinger et al. | |
| 2013/0196840 A1 | 8/2013 | Pieper et al. | |
| 2019/0201916 A1 | 7/2019 | Min et al. | |

FOREIGN PATENT DOCUMENTS

| | | |
|---|---|---|
| WO | WO 98/50163 A1 | 11/1998 |
| WO | WO 99/11305 A1 | 3/1999 |
| WO | WO 00/54823 A1 | 9/2000 |
| WO | WO 01/24848 A1 | 4/2001 |
| WO | WO 01/66172 A2 | 9/2001 |
| WO | WO 2005/003738 A2 | 1/2005 |
| WO | WO 2006/071496 A2 | 7/2006 |
| WO | WO 2007/143386 A2 | 12/2007 |
| WO | WO 2008/140561 A1 | 11/2008 |
| WO | WO 2008/156906 A1 | 12/2008 |
| WO | WO 2010/014330 A2 | 2/2010 |
| WO | WO 2010/019317 A2 | 2/2010 |
| WO | WO 2010/019318 A1 | 2/2010 |
| WO | WO 2010/030406 A1 | 3/2010 |
| WO | WO 2021/194824 A1 | 9/2021 |

OTHER PUBLICATIONS

Partial European Search Report (R. 64 EPC), dated Jul. 27, 2022, for application No. EP22166498.0-1113.

* cited by examiner

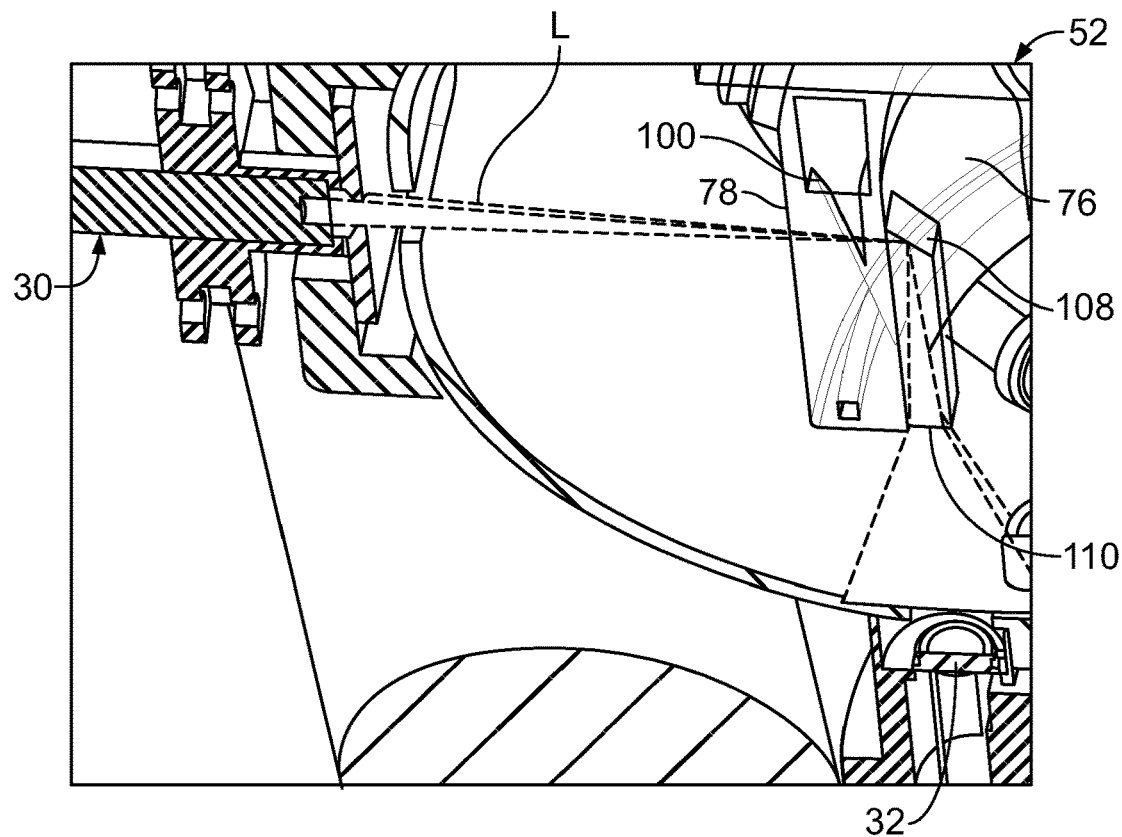
FIG. 4
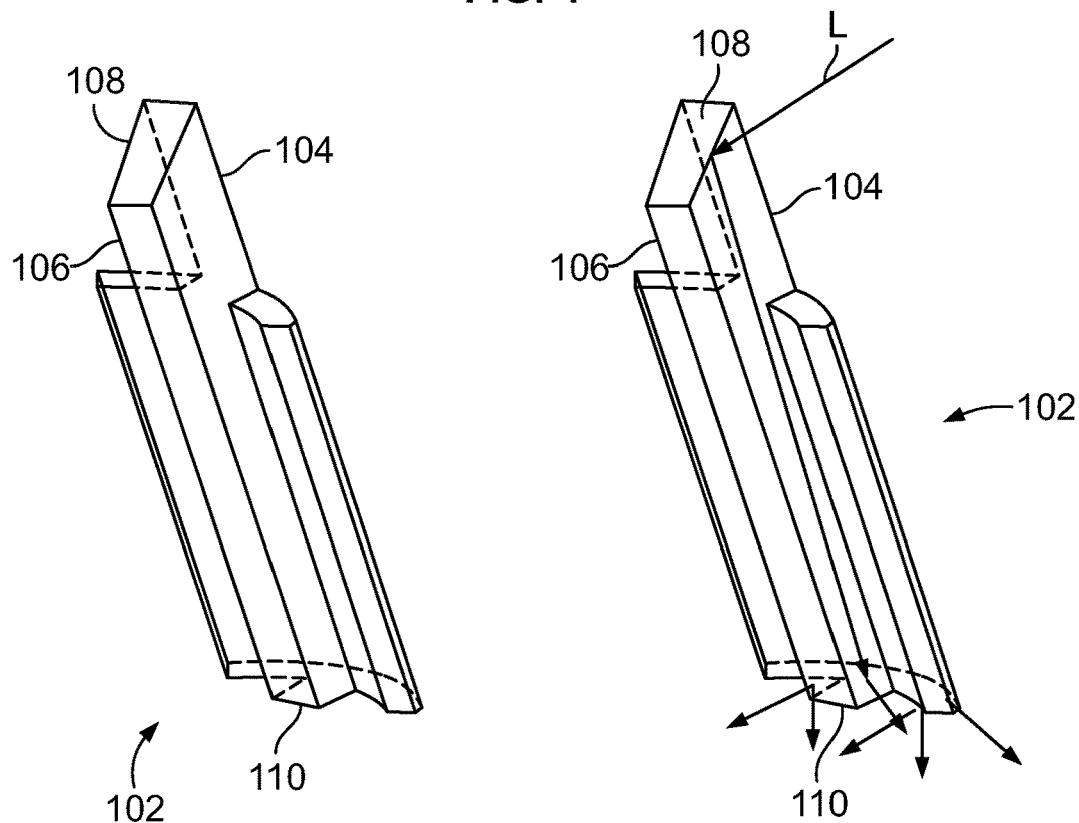
FIG. 12  FIG. 13

CONTINUOUS FLOW CENTRIFUGATION CHAMBERS

CROSS-REFERENCE TO RELATED APPLICATIONS

This application claims the benefit of and priority of U.S. Provisional Patent Application Ser. Nos. 63/170,678, filed Apr. 5, 2021; 63/211,652, filed Jun. 17, 2021; and 63/296,532, filed Jan. 5, 2022, the contents of which are incorporated by reference herein.

BACKGROUND

Field of the Disclosure

The disclosure relates to centrifugation systems. More particularly, the disclosure relates to continuous flow centrifugation chambers for use in centrifugation systems.

Description of Related Art

A wide variety of fluid processing systems are presently in practice and allow for a fluid to be fractionated or separated into its constituent parts. For example, various blood processing systems make it possible to collect particular blood constituents, rather than whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor or patient, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents through centrifugation. In continuous processes, this requires that the whole blood be passed through a centrifuge after it is withdrawn from, and before it is returned to, the blood source. To avoid contamination and possible infection (if the blood source is a human donor or patient), the blood is preferably contained within a preassembled, sterile fluid flow circuit or system during the entire centrifugation process. Typical blood processing systems thus include a permanent, reusable module or assembly containing the durable hardware (centrifuge, drive system, pumps, valve actuators, programmable controller, and the like) that controls the processing of the blood and blood components through a disposable, sealed, and sterile flow circuit that includes a centrifugation chamber and is mounted in cooperation on the hardware.

The hardware engages and spins the disposable centrifugation chamber during a blood separation step. As the flow circuit is spun by the centrifuge, the heavier (greater specific gravity) components of the whole blood in the flow circuit, such as red blood cells, move radially outwardly away from the center of rotation toward the outer or "high-G" wall of the centrifugation chamber. The lighter (lower specific gravity) components, such as plasma, migrate toward the inner or "low-G" wall of the centrifuge. Various ones of these components can be selectively removed from the whole blood by providing appropriately located outlet ports in the flow circuit.

Centrifugation chambers of this type are well-known, with exemplary centrifugation chambers being described in U.S. Pat. No. 9,327,296 and U.S. Patent Application Publication No. 2019/0201916, the disclosures of both of which are hereby incorporated herein by reference. While conventional centrifugation chambers have proven to be suitable for separation blood and other biological fluids, it would be advantageous to provide chambers improving on the performance of such known chambers. This could include improvements to the purity of the fluid components that are produced by such chambers and/or improvements to the monitoring of various aspects of the flow of fluid through such chambers.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid separation chamber for rotation about an axis includes a central hub coinciding with the axis. A generally annular low-G wall and a generally annular high-G wall extend about the central hub in a spaced apart relationship to define therebetween a separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages that open into the separation channel at a bottom end of the separation channel. A bottom end of the high-G wall has an at least substantially uniform radius from the upstream end of the separation channel to the downstream end of the separation channel, while a bottom end of the low-G wall includes an air drain taper having a width that increases from the upstream end of the separation channel to the downstream end of the separation channel so as to decrease the radius of the bottom end of the low-G wall from the upstream end of the separation channel to the downstream end of the separation channel and increase a width of the bottom end of the separation channel from the upstream end of the separation channel to the downstream end of the separation channel.

In another aspect, a fluid separation chamber for rotation about an axis includes a central hub coinciding with the axis, with a generally annular low-G wall and a generally annular high-G wall extending about the central hub in a spaced apart relationship to define therebetween a separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. The high-G wall has an at least substantially uniform radius from the upstream end of the separation channel to the downstream end of the separation channel at each axial position, while the low-G wall has a radius that decreases from the upstream end of the separa- tion channel to the downstream end of the separation channel at each axial position so as to increase a width of the separation channel from the upstream end of the separation channel to the downstream end of the separation channel at each axial position.

In yet another aspect, a fluid separation chamber for rotation about an axis includes a central hub coinciding with the axis, with a generally annular low-G wall and a generally annular high-G wall extending about the central hub in a spaced apart relationship to define therebetween a separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages opening into the separation channel at a bottom end of the separation channel. A ramp extends generally diagonally across the separation channel from the high-G wall at a first position to the low-G wall at a second position downstream of the first position, with a portion of the ramp extending to the bottom end of the separation channel.

In another aspect, a fluid separation chamber for rotation about an axis includes a central hub coinciding with the axis, with a generally annular low-G wall and a generally annular high-G wall extending about the central hub in a spaced apart relationship to define therebetween a separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. The low-G wall includes a generally planar extension at the downstream end of the separation channel, with a portion of the extension extending along an entire height of the separation channel. The extension extends from a first end to a second end downstream of the first end. The low-G wall has a smaller radius at the second end than at the first end, and the low-G outlet passage opens into the separation channel at the second end of the extension.

In yet another aspect, a fluid separation chamber for rotation about an axis includes a central hub coinciding with the axis, with a generally annular low-G wall and a generally annular high-G wall extending about the central hub in a spaced apart relationship to define therebetween a separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. A ramp extends generally diagonally across the separation channel from the high-G wall at a first position to the low-G wall at a second position downstream of the first position, with the ramp being positioned at the downstream end of the separation channel.

In another aspect, a fluid separation chamber for rotation about an axis includes a central hub coinciding with the axis, with a generally annular low-G wall and a generally annular high-G wall extending about the central hub in a spaced apart relationship to define therebetween a separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. A ramp extends generally diagonally across the separation channel from the high-G wall at a first position to the low-G wall at a second position downstream of the first position, with the high-G outlet passage opening into the separation channel at the first position of the ramp.

In yet another aspect, a fluid separation chamber for rotation about an axis includes a central hub coinciding with the axis, with a generally annular low-G wall and a generally annular high-G wall extending about the central hub in a spaced apart relationship to define therebetween a single-stage separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. The high-G wall and the low-G wall each have a radius that decreases from the upstream end of the separation channel to the downstream end of the separation channel at each axial position, with a width of the separation channel being at least substantially uniform from the upstream end of the separation channel to the downstream end of the separation channel at each axial position.

In another aspect, a fluid separation chamber for rotation about an axis includes a central hub coinciding with the axis, with a generally annular low-G wall and a generally annular high-G wall extending about the central hub in a spaced apart relationship to define therebetween a separation channel having an upstream end, a downstream end, a top end, and a bottom end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. The inlet passage opens into the separation channel at the top end of the separation channel, while the high-G outlet passage opens into the separation channel at the bottom end of the separation channel, at the upstream end of the separation channel.

In yet another aspect, a fluid separation chamber for rotation about an axis includes a central hub coinciding with the axis, with a generally annular low-G wall and a generally annular high-G wall extending about the central hub in a spaced apart relationship to define therebetween a single-stage separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. The inlet passage opens into the separation channel at the top end of the separation channel, while the high-G outlet passage opens into the separation channel at the bottom end of the separation channel, at the upstream end of the separation channel. The high-G wall and low-G wall each have a radius that decreases from the upstream end of the separation channel to the downstream end of the separation channel at each axial position, with a width of the separation channel being at least substantially uniform from the upstream end of the separation channel to the downstream end of the separation channel at each axial position.

In another aspect, a fluid separation chamber for rotation about an axis includes a central hub coinciding with the axis, with a generally annular low-G wall and a generally annular high-G wall extending about the central hub in a spaced apart relationship to define therebetween a separation channel having an upstream end and a downstream end. A plurality of radial walls extend from the central hub to the separation channel to define a terminal wall separating the upstream end of the separation channel from the downstream end of the separation channel, an inlet passage at the upstream end of the separation channel, and low-G and high-G outlet passages. First and second ramps each extend generally diagonally across the separation channel, with the first ramp being positioned at the downstream end of the separation channel and the second ramp being positioned at the upstream end of the separation channel.

In yet another aspect, a method is provided for determining a radial position of an interface between separated fluid components within a separation channel of a fluid separation chamber. The method includes optically detecting a first radial position of the interface between separated fluid components within the separation channel at a downstream end of the separation channel and optically detecting a second radial position of the interface between separated fluid components within the separation channel at an upstream end of the separation channel. The radial position of the interface is then determined based on at least one of the first and second radial positions.

In another aspect, an interface monitoring system for determining a radial position of an interface between separated fluid components within a separation channel of a fluid separation chamber includes a light source configured to transmit a light into the fluid separation chamber and through the separation channel at downstream and upstream ends of the separation channel. A light detector is configured to receive at least a portion of the light transmitted through the downstream end of the separation channel and generate a first signal indicative of a first radial position of the interface at the downstream end of the separation channel and to receive at least a portion of the light transmitted through the upstream end of the separation channel and generate a second signal indicative of a second radial position of the interface at the upstream end of the separation channel. A controller is configured to receive the first and second signals and determine the radial position of the interface based on at least one of the first and second signals.

These and other aspects of the present subject matter are set forth in the following detailed description of the accompanying drawings.

BRIEF DESCRIPTION OF THE DRAWINGS

FIG. 4 is a perspective view of the centrifuge of FIG. 3, with selected portions thereof broken away to show the light source and light detector of an optical system;

FIG. 12 is a perspective view of an exemplary prismatic reflector suitable for use with or incorporation into a fluid processing chamber according to the present disclosure;

FIG. 13 is a perspective view of the prismatic reflector of FIG. 12, showing light being transmitted therethrough;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
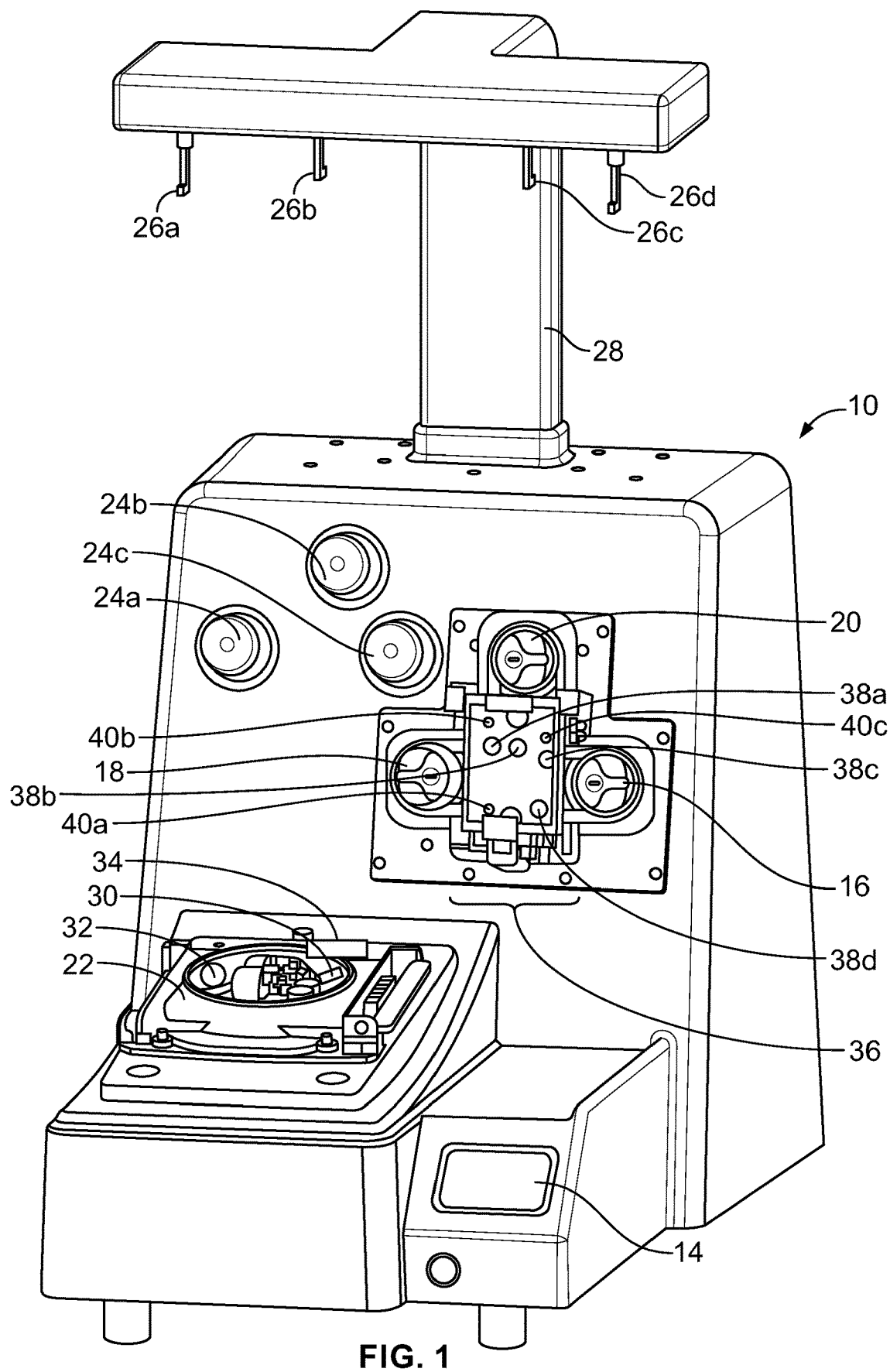
FIG. 1 is a perspective view of an exemplary reusable hardware component of a fluid processing system which is configured to receive a disposable fluid flow circuit.

FIG. 1 depicts an exemplary reusable or durable hardware component or processing device 10 that may be used in combination with a disposable or single use fluid flow circuit 12 (FIG. 2) that includes (among other components) a fluid separation chamber according to the present disclosure. The illustrated processing device 10 includes associated pumps, valves, sensors, displays, and other apparatus for configuring and controlling flow of fluid through the fluid flow circuit 12. The processing device 10 may be directed by a controller integral with the processing device 10 that includes a programmable microprocessor to automatically control the operation of the pumps, valves, sensors, etc. The processing device 10 may also include wireless communication capabilities to enable the transfer of data from the processing device 10 to the quality management systems of the operator.

Figure 3:
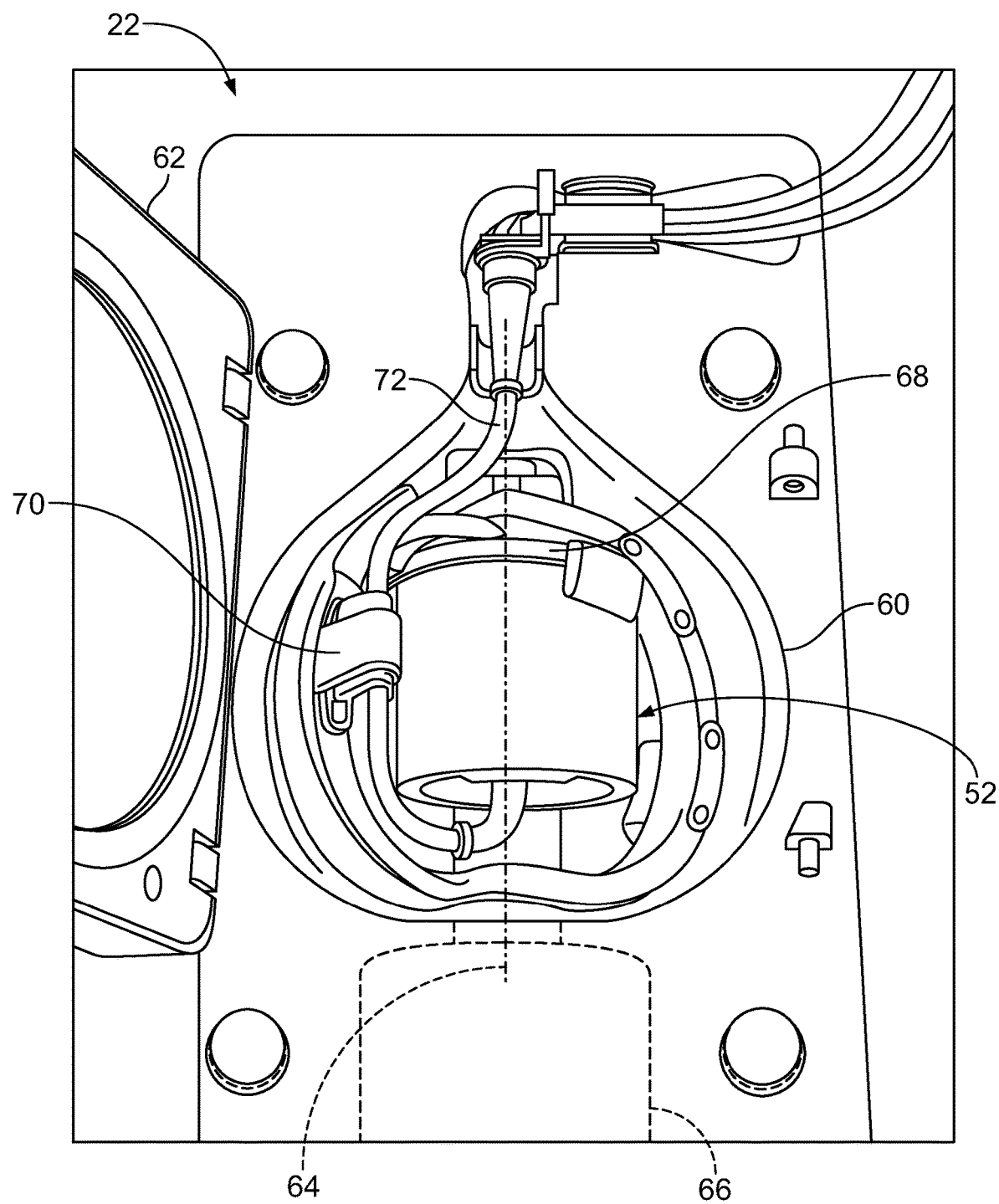
FIG. 3 is a perspective view of an exemplary centrifuge of the fluid processing device of FIG. 1, with the fluid separation chamber of a fluid flow circuit mounted therein.

In the illustrated embodiment, the processing device 10 includes a user input and output touchscreen 14, a pump station or system including a first pump 16 (for pumping, e.g., whole blood), a second pump 18 (for pumping, e.g., plasma) and a third pump 20 (for pumping, e.g., additive solution), a centrifuge mounting station and drive unit 22 (which may be referred to herein as a "centrifuge" and is shown in greater detail in FIG. 3), and clamps 24a-c. The touchscreen 14 enables user interaction with the processing device 10, as well as the monitoring of procedure parameters, such as flow rates, container weights, pressures, etc. The pumps 16, 18, and 20 (collectively referred to herein as being part of a "pump system" of the processing device 10) are illustrated as peristaltic pumps capable of receiving tubing or conduits of the fluid flow circuit 12 and moving fluid at various rates through the associated conduit dependent upon the procedure being performed. An exemplary centrifuge mounting station/drive unit is seen in U.S. Pat. No. 8,075,468 (with reference to FIGS. 26-28), which is hereby incorporated herein by reference. The clamps 24a-c (collectively referred to herein as being part of the "valve system" of the processing device 10) are capable of opening and closing fluid paths through the tubing or conduits and may incorporate RF sealers in order to complete a heat seal of the tubing or conduit placed in the clamp to seal the tubing or conduit leading to a product container upon completion of a procedure.

The processing device 10 also includes hangers 26a-d (which may each be associated with a weight scale) for suspending the various containers of the fluid flow circuit 12. The hangers 26a-d are shown as being mounted to a support 28, which is vertically translatable to improve the transportability of the processing device 10. An optical system (shown in greater detail in FIG. 4) comprising a light source 30 (which may be configured as a laser, for example) and a light detector 32 (which may be configured as a photodiode, for example) is associated with the centrifuge 22 for determining and controlling the location of an interface between separated fluid components within the centrifuge 22. An exemplary optical system is shown in U.S. Patent Application Publication No. 2019/0201916. An optical sensor 34 is also provided to optically monitor one or more conduits leading into or out of the centrifuge 22.

The face of the processing device 10 includes a nesting module 36 for seating a flow control cassette 50 (FIG. 2) of the fluid flow circuit. The cassette nesting module 36 is configured to receive various disposable cassette designs so that the system may be used to perform different types of procedures. Embedded within the illustrated cassette nesting module 36 are four valves 38a-d (collectively referred to herein as being part of the "valve system" of the processing device 10) for opening and closing fluid flow paths within the flow control cassette 50, and three pressure sensors 40a-c capable of measuring the pressure at various locations of the fluid flow circuit 12.

Figure 2:
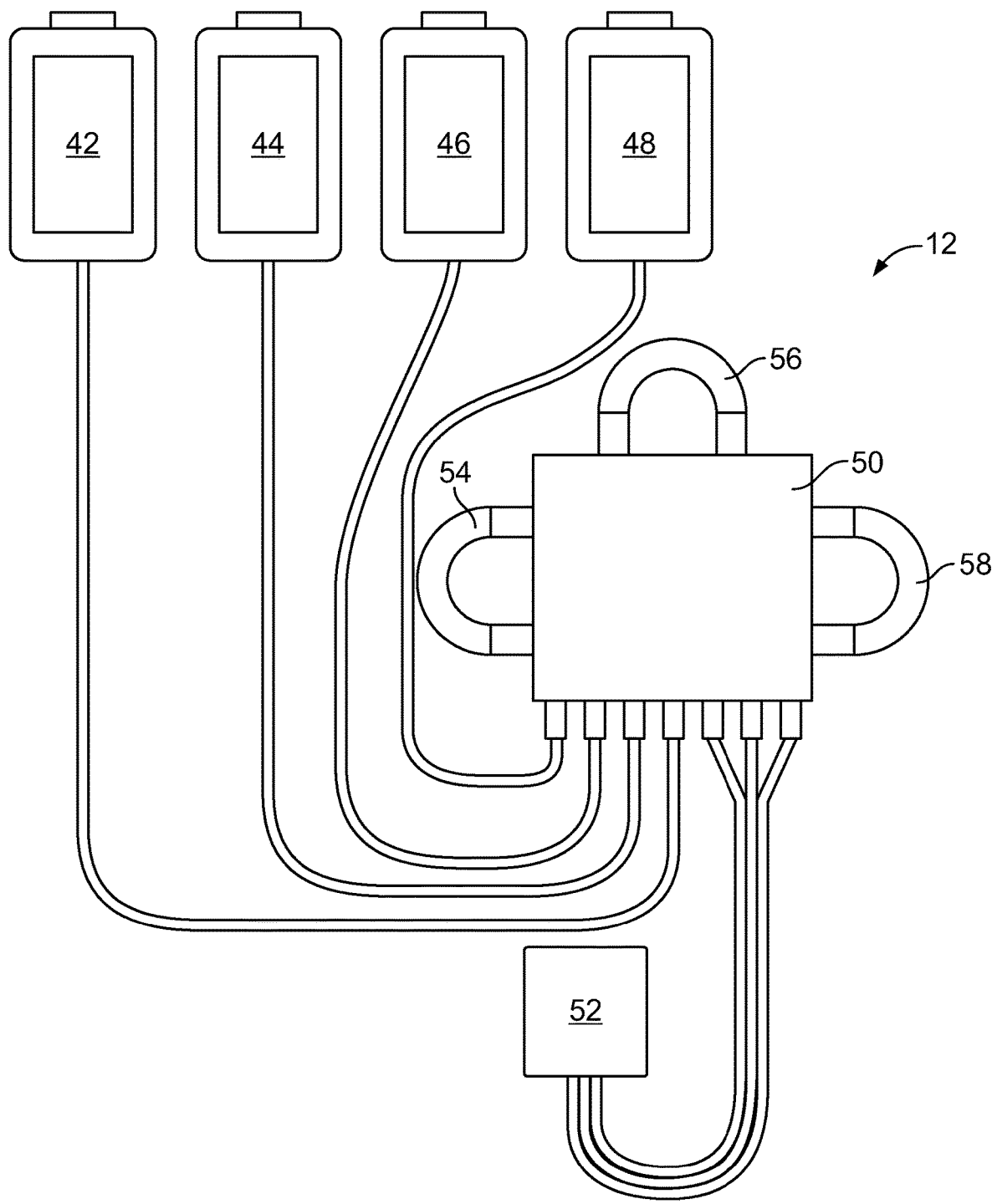
FIG. 2 is a plan view of an exemplary disposable fluid flow circuit for use in combination with the durable hardware component of FIG. 1.

With reference to FIG. 2, the illustrated fluid flow circuit 12 includes a plurality of containers 42, 44, 46, and 48, with a flow control cassette 50 and a fluid separation chamber 52 that is configured to be received in the centrifuge 22, all of which are interconnected by conduits or tubing segments, so as to permit continuous flow centrifugation. The flow control cassette 50 routes the fluid flow through three tubing loops 54, 56, 58, with each loop being positioned to engage a particular one of the pumps 16, 18, 20. The conduits or tubing may extend through the cassette 50, or the cassette 50 may have pre-formed fluid flow paths that direct the fluid flow.

In the fluid flow circuit 12 shown in FIG. 2, container 42 may be pre-filled with additive solution, container 44 may be filled with a fluid to be separated (e.g., whole blood) and connected to the fluid flow circuit 12 at the time of use, container 46 may be an empty container for the receipt of a first component (e.g., red blood cells) separated from the fluid, and container 48 may be an empty container for the receipt of a second component (e.g., plasma) separated from the fluid. While FIG. 2 shows a container 44 as a fluid source, it is within the scope of the present disclosure for the fluid source to be a living donor (in the case of blood separation).

Figure 5:
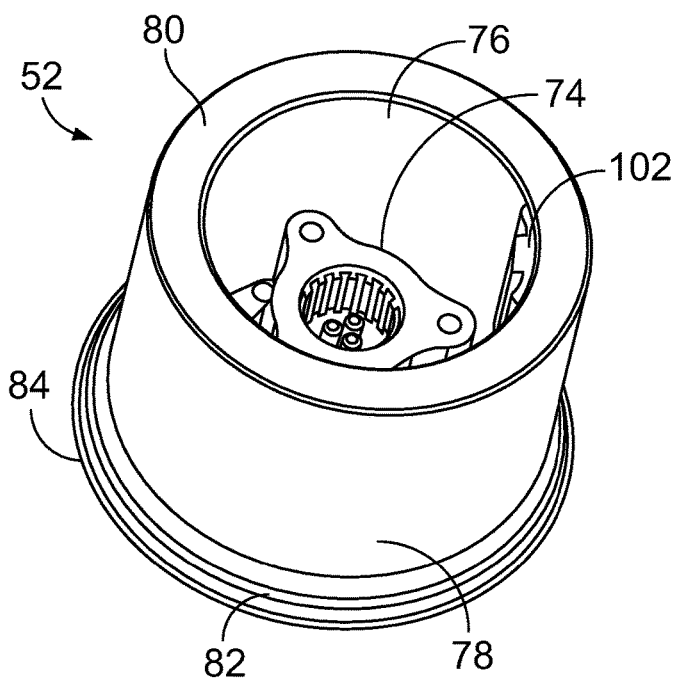
FIG. 5 is a perspective view of an exemplary fluid processing chamber suitable for mounting within the centrifuge of FIG. 3.
Figure 6:
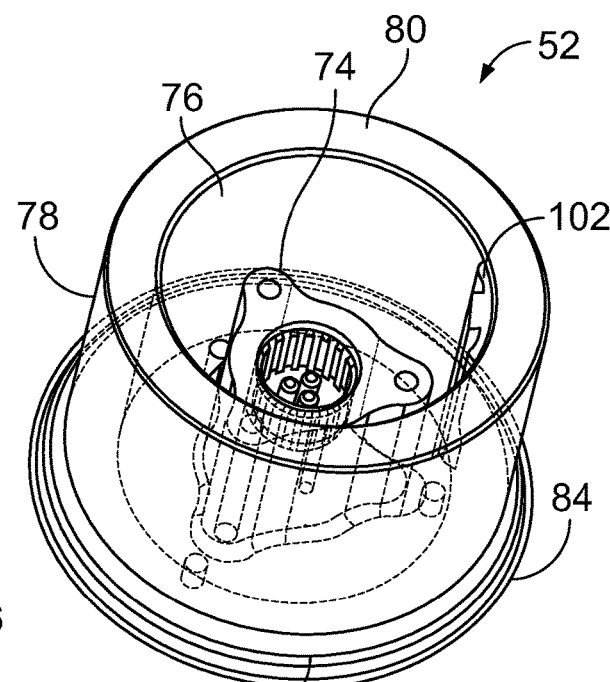
FIG. 6 is a perspective view of the fluid processing chamber of FIG. 5, showing interior details of the chamber.
Figure 7:
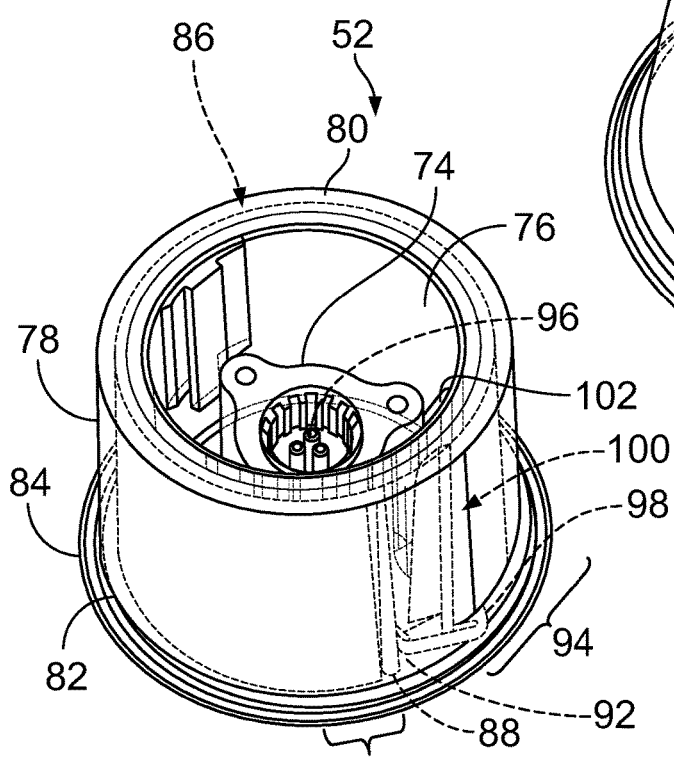
FIG. 7 is a perspective view of the fluid processing chamber of FIG. 5, showing fluid flow through the chamber.

FIGS. 5-7 illustrate an exemplary fluid separation chamber 52, with FIG. 5 showing the chamber 52, FIG. 6 showing interior details of the chamber 52, and FIG. 7 showing the position of various fluid components within the chamber 52 during an exemplary fluid separation procedure. The chamber 52 may be pre-formed in a desired shape and configuration by injection molding from a rigid plastic material, as shown and described in U.S. Pat. No. 6,849,039, which is hereby incorporated herein by reference. In some embodiments, it may be advantageous for the chamber 52 to be formed of a generally translucent or transparent material to allow for optical monitoring of fluid flow through the chamber 52, as will be described in greater detail herein. Different possible configurations of the chamber 52 will also be described in greater detail herein.

Briefly, the controller of the processing device 10 is pre-programmed to automatically operate the system to perform one or more standard fluid separation or processing procedures selected by an operator by input to the touchscreen 14, and may be configured to be further programmed by the operator to perform additional separation and processing procedures. The controller commands the other components of the processing device 10 at pre-set settings for flow rates, centrifugation forces, etc., and may be further configured to receive input from the operator as to one or more parameters to override or supplement the pre-programmed settings. The controller may be pre-programmed to substantially automate a wide variety of procedures, including, but not limited to: red blood cell and plasma production from whole blood, buffy coat pooling, buffy coat separation into a platelet product, glycerol addition to red blood cells, red blood cell washing, platelet washing, and cryoprecipitate pooling and separation. Chambers according to the present are particularly well-suited for separating blood into two or more components (e.g., for collecting a red blood cell product and a plasma product or a red blood product, a plasma product, and a buffy coat product from a single unit of blood) and will be described in the context of blood separation. However, it should be understood that chambers according to the present disclosure may be used to separate other fluids, including both biological/bodily fluids and non-biological fluids.

Turning now more particularly to the centrifuge 22 (FIG. 4), it includes a centrifuge compartment 60 that may receive the other components of the centrifuge 22. The centrifuge compartment 60 may include a lid 62 that is opened to insert and remove a chamber 52 of the fluid flow circuit 12. During a separation procedure, the lid 62 may be closed with the chamber 52 positioned within the centrifuge compartment 60, as the chamber 52 is spun or rotated about an axis 64 under the power of an electric drive motor or rotor 66 of the centrifuge 22.

The particular configuration and operation of the centrifuge 22 depends upon the particular configuration of the chamber 52 of the fluid flow circuit 12. In the illustrated embodiment, the centrifuge 22 may include a carriage or support 68 that holds the chamber 52 and a yoke member 70. The yoke member 70 engages an umbilicus 72 of the fluid flow circuit 12, which extends between the chamber 52 and the cassette 50 (FIG. 2). The yoke member 70 causes the umbilicus 72 to orbit around the chamber 52 at a "one-omega" rotational speed. The umbilicus 72 twists about its own axis as it orbits around the chamber 52. The twisting of the umbilicus 72 about its axis as it rotates at one-omega with the yoke member 70 imparts a "two-omega" rotation to the chamber 52, according to known design. The relative rotation of the yoke member 70 at a one-omega rotational speed and the chamber 52 at a two-omega rotational speed keeps the umbilicus 72 untwisted, avoiding the need for rotating seals.

Fluid is introduced into the chamber 52 by the umbilicus 72, with the fluid being separated into a layer of less dense components (such as plasma) and a layer of more dense components (such as packed red blood cells) within the chamber 52 as a result of centrifugal forces as it rotates. As will be described in greater detail, additional component layers may arise between the layers of the most- and least-dense components. The optical system positioned within the centrifuge compartment 60 oversees separation of the fluid within the chamber 52. As shown in FIG. 4, the optical system includes a light source 30 and a light detector 32, which is positioned and oriented to receive at least a portion of the light "L" emitted by the light source 30. In the illustrated embodiment, the light source 30 and the light detector 32 are positioned on stationary surfaces of the centrifuge compartment 60 but, in other embodiments, one or both may be mounted to a movable component of the centrifuge 22 (e.g., to the yoke member 70, which rotates at a one-omega speed). It is also within the scope of the present disclosure for the optical system to be omitted, particularly when the chamber 52 is formed of an opaque material that does not transmit light therethrough.

The orientation of the various components of the optical system depends at least in part on the particular configuration of the chamber 52, which will be described in greater detail herein. In general, though, the light source 30 emits a light beam L (e.g., a laser light beam) through the separated fluid components within the chamber 52 (which may be formed of a material that substantially transmits the light or at least a particular wavelength of the light without absorbing it). A portion of the light L reaches the light detector 32, which transmits a signal to the controller that is indicative of the location of an interface between the separated fluid components. If the controller determines that the interface is in the wrong location (which can affect the separation efficiency of the centrifuge 22 and/or the quality of the separated fluid components), then it can issue commands to the appropriate components of the processing device 10 to modify their operation so as to move the interface to the proper location.

A central hub 74 of the chamber 52 (FIGS. 5-7) coincides with the rotational axis 64 when the chamber 52 is mounted within the centrifuge 22. The central hub 74 includes a shaped receptacle that is suitable for receiving an end of the umbilicus 72 of the fluid flow circuit 12. A suitable receptacle and the manner in which the umbilicus 72 may cooperate with the receptacle to deliver fluid to and remove fluid from the chamber 52 are described in greater detail in U.S. Pat. No. 8,075,468.

The illustrated chamber 52 has generally annular, radially spaced apart inner (low-G) and outer (high-G) walls 76 and 78 extending about the central hub 74. The body of the chamber 52 further includes a top end 80 and a bottom end 82. It should be understood that the terms "top" and "bottom" are not intended to restrict the structure or orientation of the chamber 52 (e.g., FIG. 3 shows the bottom end 82 positioned above the top end 80), but rather are used to describe the various components of the chamber 52 in the orientation of FIGS. 5-7. A cover 84 is associated with the bottom end 82 (which is formed as an open surface), with the cover 84 comprising a simple flat part that can be easily welded or otherwise secured to the body of the chamber 52. Because all features that affect the separation process are incorporated into one injection molded component, any tolerance differences between the cover 84 and the body of the chamber 52 will not affect the separation efficiencies of the chamber 52. The low- and high-G walls 74 and 76, the top end 80, and the cover 84 together define an enclosed, generally annular separation channel 86 (FIG. 7), with the cover defining the bottom end of the separation channel 86.

A plurality of radial walls extend from the central hub 74 to the separation channel 86, with two of the radial walls defining an inlet passage 88 opening into the separation channel 86 at an upstream end 90 of the separation channel 86. One of the radial walls 92 (which may define a surface of the inlet passage 88 and may be referred to as the "terminal wall") joins the high-G wall 78 and separates the upstream end 90 of the channel 86 from a downstream end 94. As used herein, the terms "upstream end" and "downstream end," when used in regard to regions of the separation channel 86, may refer to the first quarter or quadrant of the channel 86 (i.e., the region encompassing approximately 90° of the channel 86 on the side of the terminal wall 92 in which fluid enters the channel 86) and the last quarter or quadrant of the channel 86 (i.e., the region encompassing approximately 90° of the channel 86 on the side of the terminal wall 92 opposite the upstream end of the channel 86), respectively. These terms are most frequently used herein to refer to the position of various components or formations associated with the separation channel 86 (e.g., the inlet passage 88 opens into the channel 86 at the upstream end 90 of the channel 86) such that, in certain embodiments (depending on the configurations of the components described as being present at the upstream end 90 or downstream end 94 of the separation channel 86), the terms may refer to smaller regions of the separation channel 86, which may include (for example) the term "upstream end" referring to only the first 45° or 30° or less of the channel 86 and the term "downstream end" referring to only the last 45° or 30° or less of the channel 86.

The radial walls further define low-G and high-G outlet passages 96 and 98, with the low-G outlet passage 96 opening into the channel 86 at the low-G wall 76 and the high-G outlet passage 98 opening into the channel 86 at the high-G wall 78. The illustrated outlet passages 96 and 98 are positioned at the downstream end 94 of the channel 86, such that the separated fluid components must traverse the entire length of the channel 86 before exiting the channel 86. In other embodiments, at least one of the outlet passages 96, 98 is positioned upstream of the downstream end 94 of the channel 86, which may include an outlet passage (which would most typically be the low-G outlet passage 96) positioned adjacent to the inlet passage 88 at the upstream end 90 of the channel 86.

Fluid flowed into the channel 86 separates into an optically dense layer RBC and a less optically dense layer PLS (FIG. 7) as the chamber 52 is rotated about the rotational axis 64. The optically dense layer RBC forms as larger and/or heavier fluid particles move under the influence of centrifugal force toward the high-G wall 78. In the case of blood being separated, the optically dense layer RBC will typically include red blood cells (and, hence, may be referred to herein as the "RBC layer") but, depending on the speed at which the chamber 52 is rotated, other cellular components (e.g., larger white blood cells) may also be present in the RBC layer RBC. In the case of blood being separated, the less optically dense layer PLS will include plasma (and, hence, will be referred to herein as the "plasma layer"). Depending on the speed at which the chamber 52 is rotated and the length of time that the blood is resident therein, other components (e.g., platelets and smaller white blood cells and anticoagulant) may also be present in the plasma layer PLS.

In the illustrated embodiment, fluid introduced into the channel 86 via the inlet passage 88 will travel in a generally clockwise direction (in the orientation of FIG. 7) as the RBC layer RBC separates from the plasma layer PLS. Both layers travel along the length of the channel 86, from the upstream end 90 to the downstream end 94, with the plasma layer PLS moving along the low-G wall 76 and the RBC layer RBC moving along the high-G wall 78. The plasma layer PLS eventually exits the channel 86 via the low-G outlet passage 96 (which opens into the channel 86 at the low-G wall 76) and the RBC layer RBC exiting the channel 86 via the high-G outlet passage 98 (which opens into the channel 86 at the high-G wall 78).

As the two layers PLS and ABC separate, a transition forms therebetween, which may be referred to as the interface INT. In the case of blood being separated, the buffy coat (comprised primarily of white blood cells and platelets) will be located at the interface INT, with the buffy coat building up at the downstream end 94 of the channel 86 while the plasma layer PLS and ABC layer ABC exit the channel 86 (as can be seen in FIG. 7). In blood separation procedures in which the buffy coat is to be collected, flow conditions through the channel 86 may be changed (e.g., by drawing red blood cells back into the channel 86 via the high-G outlet passage 98) to force the buffy coat out of the channel 86 (typically via the low-G outlet passage 96) for collection.

In any event, the location of the interface INT within the channel 86 can dynamically shift during blood processing, moving toward the low-G wall 76 or toward the high-G wall 78. During blood separation, if the location of the interface INT is too high (that is, if it is too close to the low-G wall 76 and the low-G outlet passage 96), red blood cells can flow into the low-G outlet passage 96, potentially adversely affecting the purity of the separated plasma. On the other hand, if the location of the interface INT is too low (that is, if it resides too far away from the low-G wall 76), the collection efficiency of the system may be impaired. The ideal or target position of the interface INT may be experimentally determined, which may vary depending on any of a number of factors (e.g., the configuration of the chamber 52, the rate at which the chamber 52 is rotated about the rotational axis 64, etc.).

As described above, the illustrated processing device 10 includes an optical system and a controller, which may include an interface control module to monitor and, as necessary, change the position of the interface INT. In embodiments including such a system, the chamber 52 is formed with a ramp 100 (FIGS. 8-11) extending generally diagonally from the high-G wall 78 at an angle across at least a portion of the channel 86. The ramp 100 may be positioned at any of a number of locations within the channel 86, with the ramp 100 being positioned at the downstream end 94 of the channel 86 in the illustrated embodiment.

The ramp 100 makes the interface INT between the RBC layer RBC and the plasma layer PLS more discernible for detection, displaying the RBC layer RBC, plasma layer PLS, and interface INT for viewing through a light-transmissive portion of the chamber 52. To that end, the ramp 100 and at least the portion of the chamber 52 angularly aligned with the ramp 100 may be formed of a light-transmissive material, although it may be advantageous for the entire chamber 52 to be formed of the same light-transmissive material.

In the illustrated embodiment, the light source 30 of the optical system is secured to a fixture or wall of the centrifuge compartment 60 and oriented to emit a light L that is directed toward the rotational axis 64 of the centrifuge 22, as shown in FIG. 4. If the light detector 32 is positioned at an angle with respect to the light source 30 (as in the illustrated embodiment), the light L emitted by the light source 30 must be redirected from its initial path before it will reach the light detector 32. In the illustrated embodiment, the light L is redirected by a reflector that is associated with a light-transmissive portion of the low-G wall 76, as shown in FIG. 4. The reflector may be a separate piece that is secured to the low-G wall 76 (e.g., by being bonded thereto) or may be integrally formed with the body of the chamber 52.

In the illustrated embodiment, the reflector is configured as described in U.S. Patent Application Publication No. 2019/0201916, as a prismatic reflector 102 (FIGS. 12 and 13), which is formed of a light-transmissive material (e.g., a clear plastic material) and has outer and inner walls 104 and 106 and first and second end walls 108 and 110. The outer wall 104 is positioned against the low-G wall 76 of the chamber 52 and is oriented substantially perpendicular to the initial path of the light L from the light source 30. This allows light L from the light source 30 to enter into the prismatic reflector 102 via the outer wall 104 while continuing along its initial path. The light L continues through the prismatic reflector 102 along its initial path until it encounters the first end wall 108. The first end wall 108 is oriented at an angle (e.g., an approximately 45° angle) with respect to the outer wall 104 and the second end wall 110, causing the light to be redirected within the prismatic reflector 102 (FIG. 13), rather than exiting the prismatic reflector 102 via the first end wall 108.

The first end wall 108 directs the light L at an angle to its initial path (which may be an approximately 90° angle, directing it from a path toward the rotational axis 64 to a path that is generally parallel to the rotational axis 64) toward the second end wall 110. The first end wall 108 and the outer and inner walls 104 and 106 of the prismatic reflector 102 may be configured to transmit the redirected light L from the first end wall 108 to the second end wall 110 by total internal reflection. The second end wall 110 is oriented substantially perpendicular to the redirected path of the light L through the prismatic reflector 102, such that the light L will exit the prismatic reflector 102 via the second end wall 110, continuing along its redirected path. In one embodiment, the second end wall 110 is roughened or textured or otherwise treated or conditioned to diffuse the light L as it exits the prismatic reflector 102, which may better ensure that the light L reaches the light detector 32 (FIG. 4).

The prismatic reflector 102 is angularly aligned with the ramp 100 (FIGS. 4 and 8-11), such that the light L from the light source 30 will only enter into the prismatic reflector 102 when the ramp 100 has been rotated into the path of the light L. At all other times (when the ramp 100 is not in the path of the light L), the light L will not reach the prismatic reflector 102 and, thus, will not reach the light detector 32. This is illustrated in FIGS. 8-11, which show the ramp 100 and prismatic reflector 102 as the chamber 52 is rotated about the rotational axis 64 (while the light source 30 remains in a fixed location).

Figure 8:
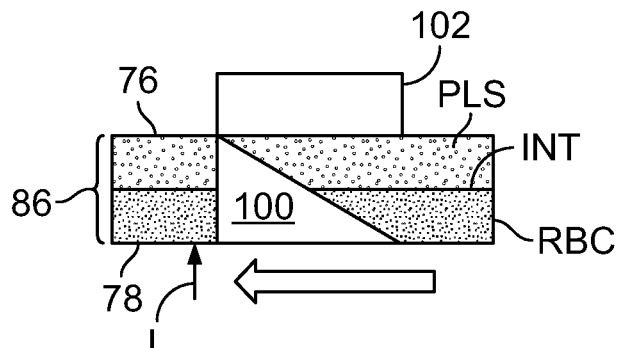
FIGS. 8-11 are diagrammatic views of a ramp and prismatic reflector of the fluid processing chamber of FIG. 5 passing through the path of light from the light source of the optical system of FIG. 4.
Figure 9:
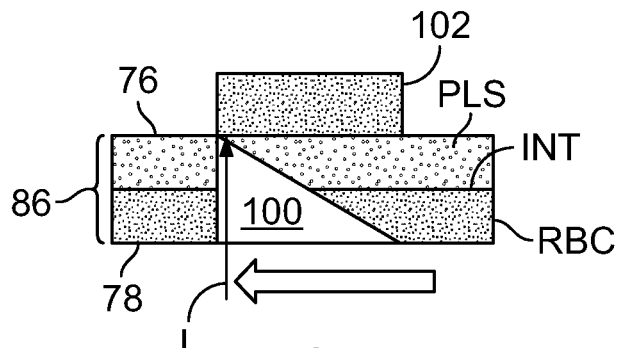

In FIG. 8, the ramp 100 and prismatic reflector 102 have not yet been rotated into the initial path of the light L from the light source 30. At this time, no light is transmitted to the light detector 32, such that the output voltage of the light detector 32 (i.e., the signal transmitted from the light detector 32 to the controller) is in a low- or zero-state. Upon the ramp 100 first being rotated into the initial path of the light L from the light source 30 (FIG. 9), the light L will pass through the ramp 100 and encounter the fluid components flowing through the channel 86, between the ramp 100 and the prismatic reflector 102. As shown in FIG. 9, the ramp 100 is oriented such that the light L passing through the ramp 100 will first encounter the plasma layer PLS within the channel 86. At least a portion of the light L will pass through the plasma layer PLS to reach the prismatic reflector 102, which directs the transmitted light to the light detector 32. At this time, the output voltage of the light detector 32 will increase, compared to the low- or zero-stage of FIG. 8.

Figure 10:
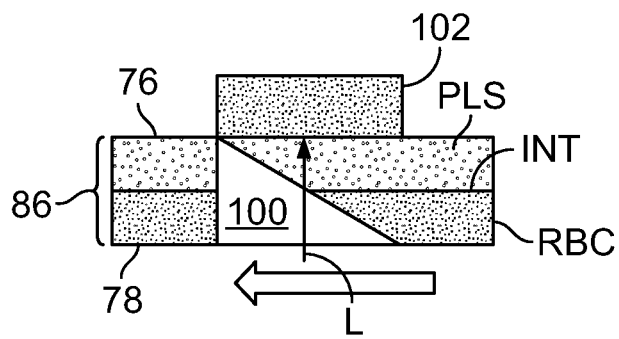

Further rotation of the ramp 100 through the path of light L from the light source 30 exposes the light L to portions of the ramp 100 that are increasingly spaced from the low-G wall 76 (i.e., the light L travels through portions of the channel 86 that are less restricted by the ramp 100 as the ramp 100 is rotated through the path of the light L). Up until the time that the interface INT on the ramp 100 is rotated into the path of the light L (as shown in FIG. 10), the only fluid in the channel 86 that the light L will have passed through will be the plasma layer PLS, such that a generally uniform level of light reaches the light detector 32 between the conditions shown in FIGS. 9 and 10. Accordingly, the voltage output of the light detector 32 will be generally uniform (at an elevated level) the whole time that the ramp 100 passes through the path of the light L before being exposed to the interface INT.

Figure 11:
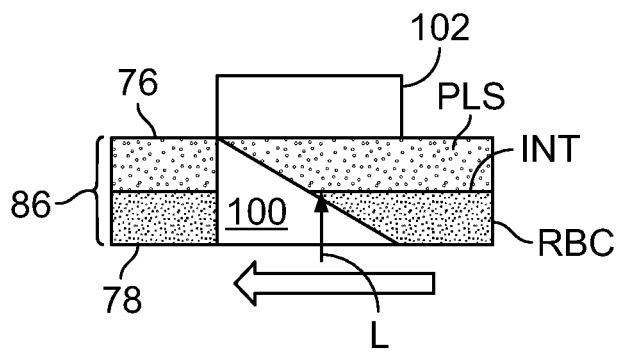

Just after the interface INT has been rotated into the path of light L from the light source 30, the light L will begin to encounter the RBC layer RBC in the channel 86, as shown in FIG. 11. As described above, the RBC layer RBC will be positioned adjacent to the high-G wall 78 as it separates from the plasma layer PLS, such that the RBC layer RBC will not be displayed on the ramp 100 until the ramp 100 is spaced a greater distance away from the low-G wall 76 (i.e., toward the right end of the ramp 100 in the orientation of FIGS. 8-11). Less light L is transmitted through the RBC layer RBC than through the plasma layer PLS (which may include all or substantially all of the light L being absorbed by the RBC layer RBC), such that the amount of light L that reaches the light detector 32 will decrease compared to the amount of light L that reaches the light detector 32 while traveling through only the plasma layer PLS in the channel 86 (FIGS. 9 and 10).

When receiving less light L, the voltage output or signal from the light detector 32 will decrease to a lower level than when the light L was passing through only the plasma layer PLS in the channel 86. When the light L encounters the RBC layer RBC in the channel 86, the light detector 32 may be generating a signal or voltage output that is approximately equal to its zero-state (as in FIG. 8, when the light detector 32 is receiving no light L) or a signal or voltage output that is some degree less than the magnitude of the signal or voltage output generated while the light L encounters only the plasma layer PLS in the channel 86. The controller may be programmed and/or configured to recognize this lower level signal as representing the presence of the RBC layer ABC on the ramp 100 (and in the portion of the channel 94 being traversed by the light L) and treat this lower level signal as the end point of the elevated signal generated by the light detector 52 while light L passes through only the plasma layer PLS in the channel 86.

Thus, the pulse width of the elevated signal from the light detector 32 to the controller (i.e., the time during which light L is traversing only the plasma layer PLS in the channel 86) is determined by the percentages of the ramp 100 that are occupied by the plasma layer PLS and the ABC layer ABC. Accordingly, a greater pulse width of the signal from the light detector 32 to the controller is associated with the plasma layer PLS occupying a larger portion of the ramp 100 and will be indicative of a thinner ABC layer ABC on the ramp 100. Conversely, a signal from the light detector 32 to the controller having a narrower pulse width is associated with the plasma layer PLS occupying a smaller portion of the ramp 100 and will be indicative of a thicker ABC layer ABC on the ramp 100 (and in the channel 86).

The controller may compare the pulse width of the signal to the pulse width generated during a calibration phase (during which the channel 86 is filled with a fluid that will transmit the light L), which corresponds to the pulse width when light L is transmitted to the light detector 32 over the entire width of the ramp 100. Comparing these two pulse widths will indicate the percentage of the ramp 100 that is occupied by the plasma layer PLS and by the ABC layer ABC, which information the controller may use to determine the location of the interface INT within the channel 86. As necessary, the controller may change flow conditions through the channel 86 (e.g., by increasing the rate at which the plasma layer PLS or the RBC layer RBC is conveyed out of the channel 86) to change the position of the interface INT within the channel 86.

As described above, the chamber 52 may be variously configured without departing from the scope of the present disclosure. FIGS. 14-33 show the fluid flow paths (i.e., the inlet passage, separation channel, and outlet passages) defined by different embodiments of chambers 52 according to the present disclosure, with the previously discussed ABC layer ABC, plasma layer PLS, and interface INT being labeled, along with the fluid to be separated being identified as "WB". While the various surfaces and formations of the chambers are not visible in FIGS. 14-33, it should be clear that the illustrated fluid flow paths are entirely defined by the corresponding chamber structures and surfaces described above (i.e., the illustrated inlet and outlet passages are defined by radial walls of the chamber, while the separation channel is defined by the low- and high-G walls, along with the ramp, if provided), as in FIG. 7 (which illustrates the chamber 52 creating the fluid flow path shown in FIGS. 26 and 27). Thus, for the sake of simplicity and brevity, when describing the fluid flow paths of FIGS. 14-33, reference may simply be made to the chamber itself and the various surfaces and formations of the chamber (e.g., stating that the chamber 52 of FIGS. 14-16 has a particularly configured ramp, rather than stating that the chamber 52 defining the fluid flow path shown in FIGS. 14-16 has a particularly configured ramp). Similarly, FIGS. 14-33 may be annotated with reference numerals (with broken lead lines) representing the chamber surface defining a particular feature of the illustrated fluid flow path, rather than employing a new reference numeral for the fluid flow path feature arising from the chamber surface (e.g., identifying a fluid flow path feature defined by the ramp 100 of a chamber 52 as the ramp 100 instead of employing a unique identifier for that region of the fluid flow path itself).

Figure 14:
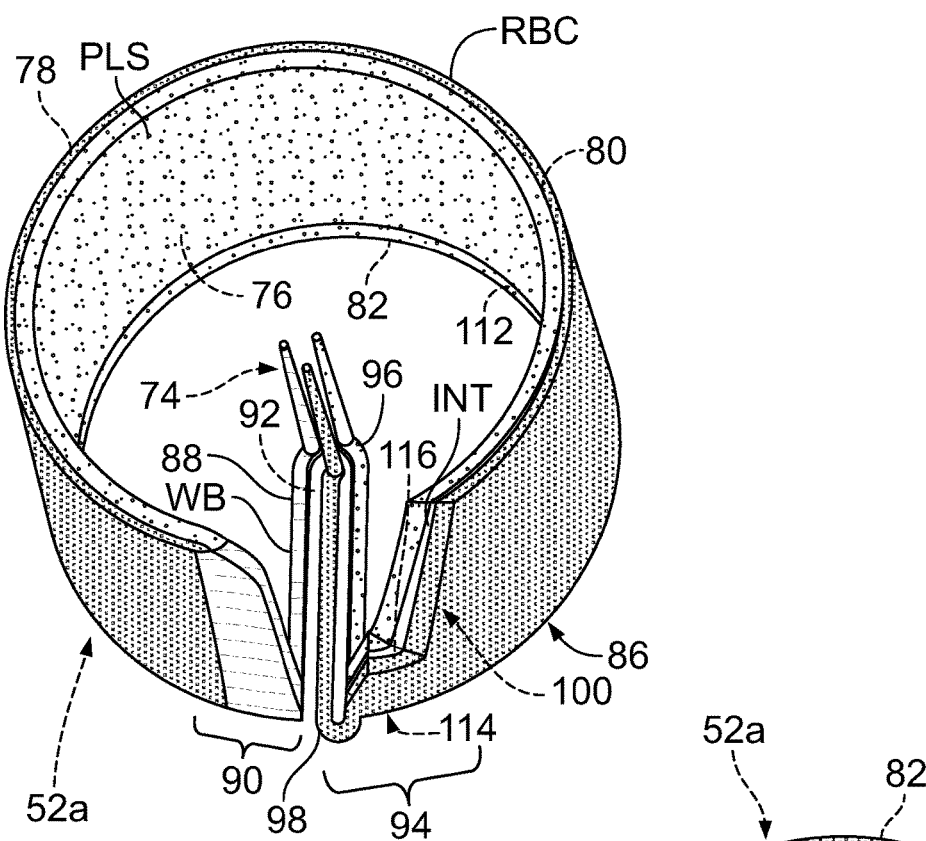
FIGS. 14 and 15 are perspective views of fluid flow through an embodiment of a fluid processing chamber according to the present disclosure.
Figure 15:
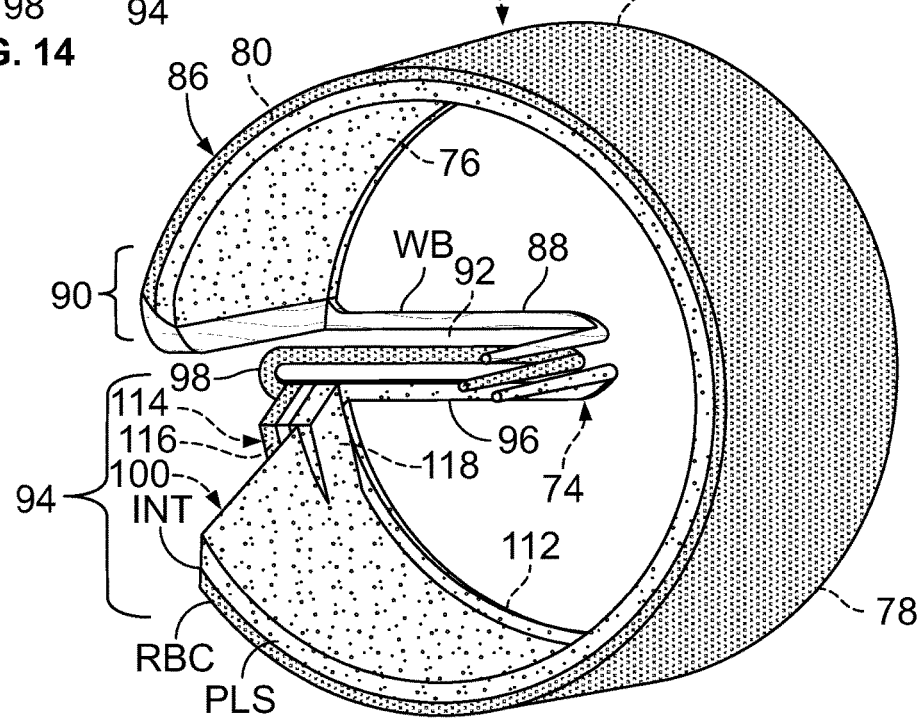
Figure 16:
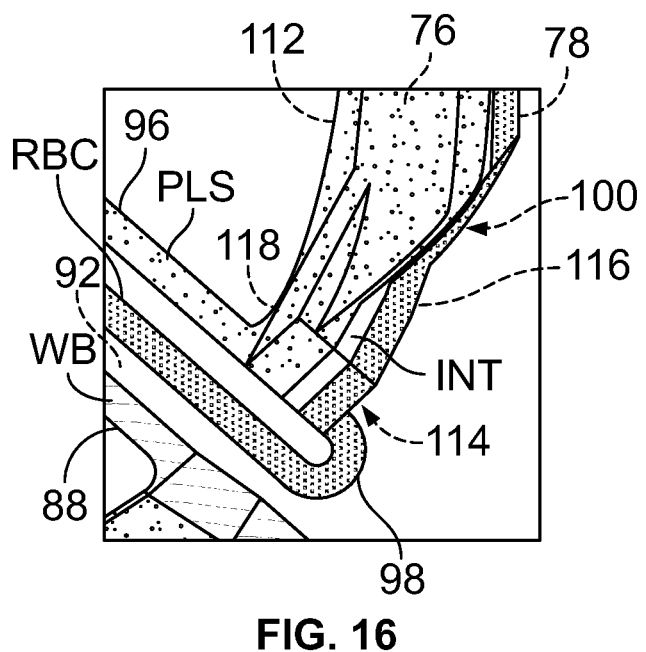
FIG. 16 is a detail view of a downstream end of the fluid flow path of FIGS. 14 and 15.
Figure 25:
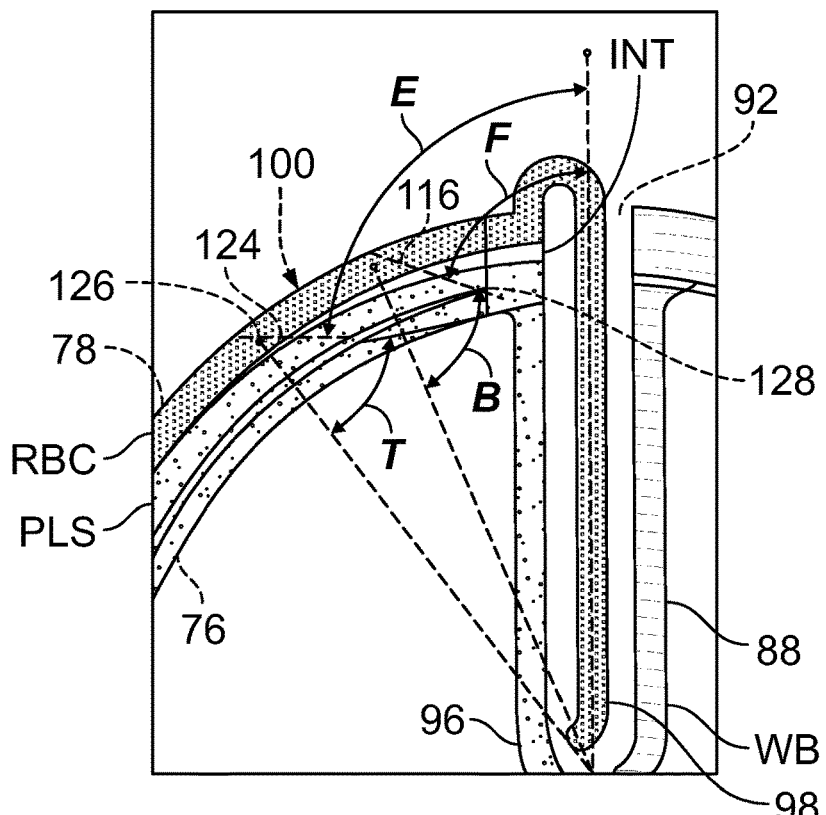
FIG. 25 is a detail view illustrating the orientation of the ramp of the fluid processing chamber defining the fluid flow path shown in FIGS. 14 and 15.
Figure 26:
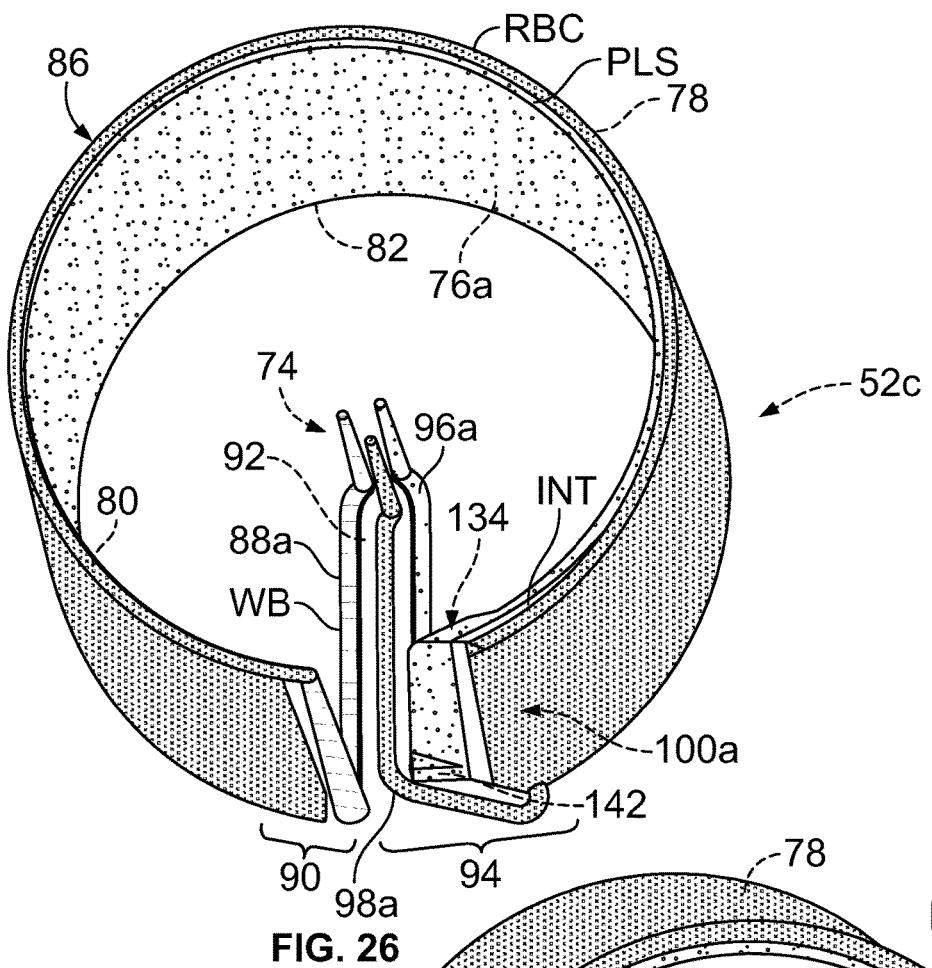
FIG. 26 is a top perspective view of fluid flow through another embodiment of a fluid processing chamber according to the present disclosure.
Figure 27:
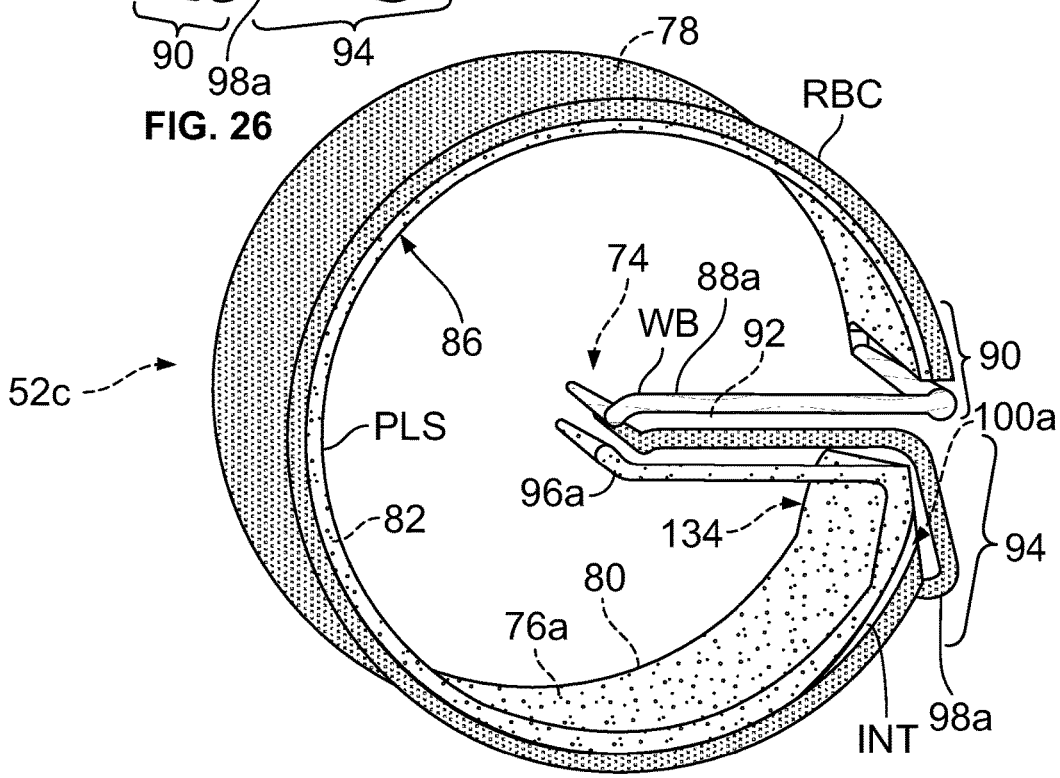
FIG. 27 is a bottom perspective view of the fluid flow path of FIG. 26.
Figure 28:
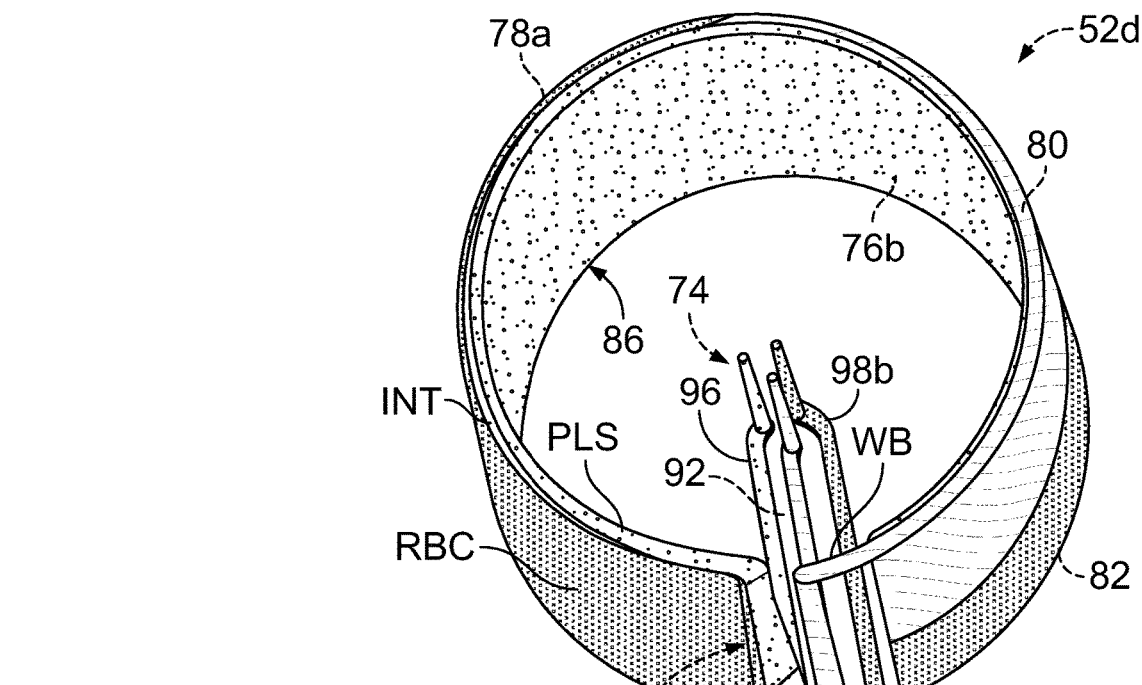
FIG. 28 is a top perspective view of fluid flow through yet another embodiment of a fluid processing chamber according to the present disclosure.

It should also be understood that the chambers 52 represented by the fluid flow paths illustrated in FIGS. 14-33 are configured and function according to the preceding description of the chamber 52 of FIGS. 5-7, except where stated to the contrary. Additionally, it should be understood that, while different features may be presented separately in the fluid flow paths shown in FIGS. 14-33 (e.g., FIGS. 14-16 illustrate a fluid flow path resulting from a chamber having a modified low-G wall, while FIGS. 26 and 27 show a fluid flow path resulting from a chamber having a modified inlet passage), the individual features of the various chambers defining those flow paths may be provided in various combinations (e.g., a chamber may incorporate the modified low-G wall of the chamber of FIGS. 14-16 and the modified inlet passage of the chamber of FIGS. 26 and 27) without departing from the scope of the present disclosure.

While the various fluid flow paths shown in FIGS. 14-33 have different features (as will be described in greater detail), their respective chambers 52 may have some commonalities. For example, in one particular embodiment, the chambers 52 are configured to be compatible with the centrifuge drive mechanism of the well-known ALYX® processing device sold by Fenwal, Inc. of Lake Zurich, Ill., which is an affiliate of Fresenius Kabi AG of Bad Homburg, Germany. In such an embodiment, the chamber 52 is configured to maximize the surface area of the separation channel 86 (i.e., maximize the surface area of the high-G wall 78). The high-G wall 78 is the separation surface area for the ABC layer ABC, such that maximizing the surface area of the high-G wall 78 will maximize the separation surface area for the ABC layer ABC. In the case of blood separation, maximizing the separation surface area for the ABC layer ABC will maximize the achievable hematocrit of the red blood cell product at a particular centrifuge rotation rate. The surface area of the high-G wall 78 is a function of the radius and height of the high-G wall 78, and it has been found that (in view of the geometric restrictions of the centrifuge drive mechanism of the ALYX® processing device) a maximum surface area in the range of 138-140 cm$^2$ is possible for the high-G wall 78 of a chamber 52 configured to be compatible with the centrifuge drive mechanism of the ALYX® processing device.

In order to enable injection molding of the chambers 52, a 1° outward taper (away from the central axis of the chamber 52, from the top end 80 to the bottom end 82) may be incorporated into the high-G wall 78, while a 1° inward taper (toward the central axis of the chamber 52, from the top end 80 to the bottom end 82) may be incorporated into the low-G wall 76. When the chamber 52 is configured to be compatible with the centrifuge drive mechanism of the ALYX® processing device, the high-G wall 78 will have (in one embodiment) a height of 6.08 cm and a radius of 4 cm at the top end 80, resulting in a radius of 4.11 cm at the bottom end 82. As will be described in greater detail, the particular configuration of the low-G walls of the chambers of FIGS. 14-27 may vary, such that the radius of the low-G wall at the top end 80 and the bottom end 82 may vary from chamber to chamber. However, regardless of the particular configuration of the low-G wall, the tapers of the low- and high-G walls (when present) will result in the separation channel 86 having a greater width at the bottom end 82 than at the top end 80. A greater channel width allows for improved fluid separation, such that the outlet passages 96, 96a and 98, 98a, 98b of all of the chambers 52 of FIGS. 14-33 are shown as opening into the separation channel 86 at the bottom end 82.

Another common feature of the fluid flow paths shown in FIGS. 14-27 (though not the fluid flow path of FIGS. 28-33) is that, in all cases, the outlet passages 96, 96a and 98, 98a defined by the chambers 52 are positioned at the downstream end 94 of the separation channel 86. This is different from the configuration of a conventional rigid chamber (e.g., as presented in U.S. Patent Application Publication No. 2019/0201916) in which the low-G outlet passage opens into the separation channel at or adjacent to the upstream end of the channel (similar to the inlet passage). Positioning both outlet passages 96, 96a and 98, 98a at the downstream end of the separation channel 86 forces the separated fluid components to traverse the entire length of the channel 86, rather than one of the fluid components reversing direction and exiting the channel at the upstream end (where the fluid enters the channel). In the case of blood separation, this configuration enables the platelets traveling in the plasma layer PLS to experience maximum residence time and separation surface area (which corresponds to the top surface of the RBC layer RBC) in order to more fully sediment them into the buffy coat/interface INT.

It will also be seen that, in all of the fluid flow paths shown in FIGS. 14-33, a ramp 100 is positioned at the downstream end 94 of the separation channel 86. This chamber configuration is different from the configuration of current rigid chambers employing a ramp (e.g., as presented in U.S. Patent Application Publication No. 2019/0201916), which positions the ramp at or adjacent to the upstream end of the separation channel (on account of the low-G outlet passage being positioned at or adjacent to the upstream end of the channel).

Turning now to the distinguishing features of the various chambers 52 represented in FIGS. 14-33, at the bottom end 82 of the chamber 52a of FIGS. 14-16, the high-G wall 78 has a uniform (or at least substantially uniform) radius, while the low-G wall 76 has a non-uniform radius at the bottom end 82 resulting from a formation 112 referred to herein as an "air drain taper." In particular, the air drain taper 112 has a width that increases from the upstream end 90 of the separation channel 86 to the downstream end 94, which has the effect of decreasing the radius of the low-G wall 76 at the bottom end 82 from the upstream end 90 of the channel 86 to the downstream end 94, with a maximum radius at the upstream end 90 and a minimum radius at the downstream end 94 (where the low-G outlet passage 96 is positioned). By such a configuration, the air drain taper 112 creates a "lowest-G" point at the bottom end 82 along the entire circumference of the separation channel 86, which is where air will tend to gather and move, thus increasing the amount of air that exits the channel 86 via the low-G outlet passage 96 during priming of the fluid flow path. An air drain taper 112 is considered to be particularly advantageous for chambers with large fluid gaps, as it enables just a small portion of the chamber to be tapered for improved air flow.

The exact configuration of the air drain taper 112 may vary without departing from the scope of the present disclosure. In one exemplary embodiment, the width of the air drain taper 112 increases gradually and uniformly from the upstream end 90 of the separation channel 86 to the downstream end 94. In this case, the air drain taper 112 may be understood as having an inner radius or surface shaped as a uniform or Archimedean spiral. In one particular embodiment (when the chamber 52a is configured to be compatible with the centrifuge drive mechanism of the ALYX® processing device), the spiral shape of the inner radius or surface of the air drain taper 112 makes 94% of a full revolution, with a pitch (offset) of 0.16 cm, resulting in a maximum radius of 3.55 cm (at the upstream end 90 of the separation channel 86) and a minimum radius of 3.4 cm (at the downstream end 94 of the channel 86). Other pitches or offsets may be employed, with the preferred pitch or offset depending on various considerations, including the resulting degree of air flow and the resulting volume of the separation channel 86 at the bottom end 82. While a uniform spiral may be advantageous for the inner radius or surface of the air drain taper 112 (to encourage uniform flow through the air drain taper 112), it should be understood that the inner radius or surface of the air drain taper 112 may follow a different path, such as the path of a non-uniform spiral.

As for the height of the air drain taper 112, it may vary without departing from the scope of the present disclosure. In one embodiment, it was found that a uniform height of 0.2 cm produced effective air flow. This height is approximately 4.2% of the height of the low-G wall 76 when the chamber 52a is configured to be compatible with the centrifuge drive mechanism of the ALYX® processing device, though it is believed that the actual height of the air drain taper 112 itself (independent of the height of the associated low-G wall 76) has a greater effect on air flow. Other heights may be employed (e.g., a height in the range of 0.15-0.25 cm), with the preferred height depending on various considerations, including the resulting degree of air flow and the resulting volume of the separation channel 86 at the bottom end 82. It should be understood that, while FIGS. 14-16 illustrate an air drain taper 112 having a uniform height, the height of the air drain taper 112 may change (typically increasing) from the upstream end 90 of the separation channel 86 to the downstream end 94.

In the illustrated embodiment, the transition between the low-G wall 76 and the air drain taper 112 is shown as a step, though it should be understood that there may instead be a smooth or gradual transition between the low-G wall 76 and the air drain taper 112. While it is not believed that providing a smooth or gradual transition will significantly affect air flow compared to a step, a smooth or gradual transition may improve the moldability of the chamber 52a.

It will be seen that, on account of the high-G wall 78 having an at least substantially uniform radius at the bottom end 82, the air drain taper 112 effectively increases the width of the separation channel 86 at the bottom end 82 from the upstream end 90 to the downstream end 94. This is in contrast to known spiral-shaped fluid flow paths (e.g., ones of the type described in U.S. Pat. No. 9,327,296) in which a low-G wall and a high-G wall both follow a spiral path from the upstream end of the separation channel to the downstream end (resulting in a uniform channel width) and known fluid separation chambers in which the width of a separation channel decreases from the upstream end to the downstream end.

In addition to the air drain taper 112, the chamber 52a of FIGS. 14-16 is also illustrated as defining a region 114 (which may be referred to as a "cell settling well") at the downstream end 94 of the separation channel 86. The bottom end 116 of the ramp 100 is entirely spaced from the bottom end 82 of the separation channel 86, with the cell settling well 114 providing a flow path extending through that space to allow the separated fluid components to reach the outlet passages 96 and 98. The surface of the cell settling well 114 closest to the center of the chamber is defined by a generally planar, radially inward departure or extension 118 of the low-G wall 76 from its standard radius (FIGS. 15 and 16), which effectively increases the width of the cell settling well 114. In the illustrated embodiment, this extension 118 has the same radius as the air drain taper 112 at the downstream end of the extension 118.

Due to the high-G wall 78 having an at least substantially uniform radius at the bottom end 82, the extension 118 effectively increases the width of the separation channel 86 at the cell settling well 114, which increases the fluid thickness and allows the plasma layer PLS to be larger at the cell settling well 114 (with the thickness of the RBC layer RBC remaining the same). In the case of blood separation, this allows the cellular content in the buffy coat/interface INT and the RBC layer RBC to be farther from the low-G outlet passage 96 at the cell settling well 114 (which is positioned directly adjacent to the openings of the outlet passages 96 and 98 into the separation channel 86). Spacing the blood cells farther from the low-G outlet passage 96 helps to prevent the cells from reaching the low-G outlet passage 96 and is particularly effective in encouraging platelets to settle in the buffy coat/interface INT. While the cell settling well 114 is shown in combination with the air drain taper 112, it should be understood that a cell settling well may be incorporated into a separation channel omitting an air drain taper.

Figure 17:
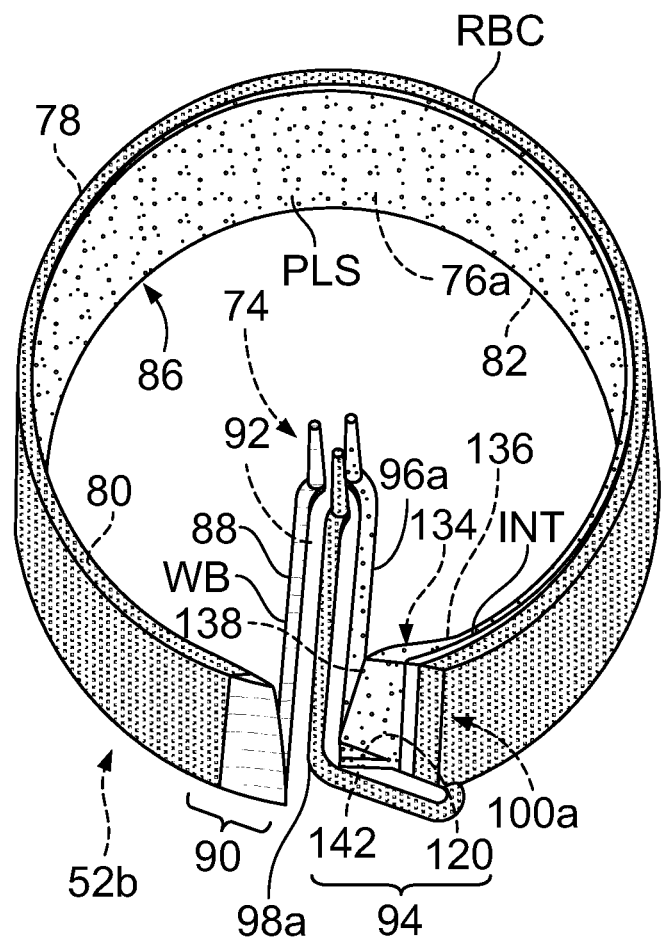
FIGS. 17 and 18 are perspective views of fluid flow through another embodiment of a fluid processing chamber according to the present disclosure.
Figure 18:
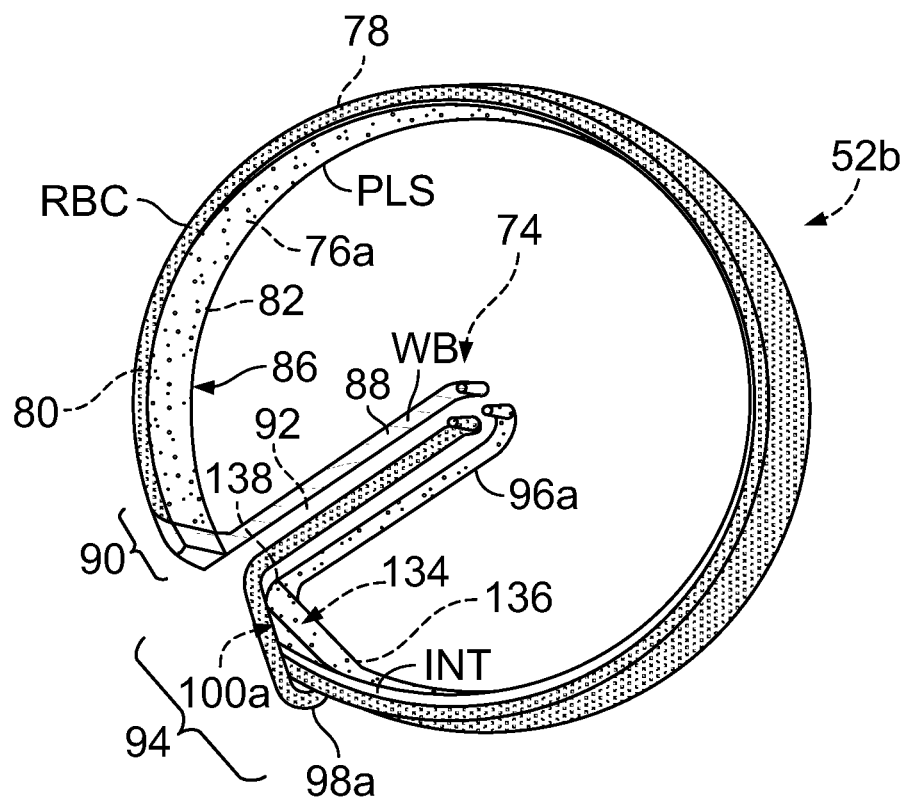
Figure 19:
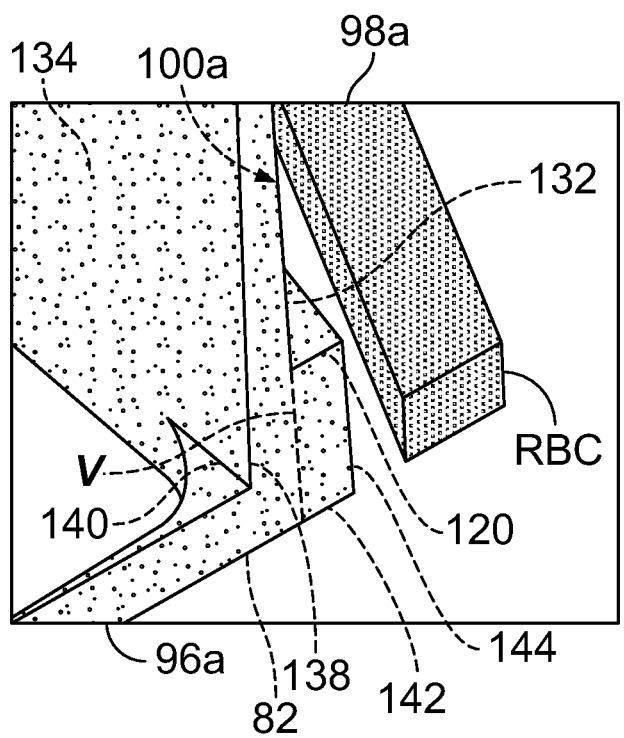
FIG. 19 is a detail view of a downstream end of the fluid flow path of FIGS. 17 and 18.

Turning now to the fluid flow path of the chamber 52b illustrated in FIGS. 17-19, it will be seen that an air drain taper is omitted. Instead, the entirety of the low-G wall 76a has a radius that decreases at each axial position from a maximum radius at the upstream end 90 of the separation channel 86 to a minimum radius at the downstream end 94. To clarify this configuration, as explained above, it may be the case that, due to manufacturing considerations (e.g., the above-described 1° inward taper), the low-G wall will not have a uniform radius along its height, instead having a greater radius at the top end of the chamber 52 than at the bottom end (for example). Thus, in the case of the chamber 52a of FIGS. 14-16, it can be said that, while the low-G wall 76 may not have a uniform radius along its height (due to manufacturing considerations), the low-G wall 76 has a uniform radius at each axial position. For example, the low-G wall 76 of the chamber 52a of FIGS. 14-16 has a uniform radius at the top end 80 of the chamber 52a and a uniform radius at the bottom end 82 of the chamber 52a, though the radii of the low-G wall 76 at the top and bottom ends 80 and 82 may be different from each other.

In contrast (and as stated above), in the embodiment of FIGS. 17-19, the low-G wall 76a has a radius that decreases at each axial position from the upstream end 90 of the separation channel 86 to the downstream end 94 of the separation channel 86. To illustrate—the top end of the low-G wall 76a of the chamber 52b of FIGS. 17-19 has a radius that decreases from a maximum radius at the upstream end 90 of the separation channel 86 (which is 3.8 cm in an exemplary embodiment) to a minimum radius at the downstream end 94 (which is 3.65 cm in the exemplary embodiment). The low-G wall 76a of FIGS. 17-19 also has a bottom end with a radius that decreases from a maximum radius at the upstream end 90 of the channel 86 to a minimum radius at the downstream end 94, though (due to manufacturing considerations) the maximum radii at the top and bottom ends may be different from each other and/or the minimum radii at the top and bottom may be different from each other. Thus, while the radius of the top end of the low-G wall 76a of FIGS. 17-19 may be different from the radius at the bottom end at any given position along the length or circumference of the separation channel 86 due to manufacturing considerations (as in the embodiment of FIGS. 14-16), at each axial position of the low-G wall 76a of FIGS. 17-19 (e.g., at each of the top and bottom ends), the radius of the low-G wall 76a at that axial position will be also different at different positions along the length or circumference of the separation channel 86. This is in contrast to the chamber 52a of FIGS. 14-16, which (as explained above) has a low-G wall 76 with a uniform radius at each axial position (i.e., a radius that may change along the height of the low-G wall 76 due to manufacturing considerations, but does not change at any given axial position along the length or circumference of the separation channel 86).

As explained above, an air drain taper may be advantageous for chambers with large fluid gaps, but the chamber 52b of FIGS. 17-19 has a smaller fluid gap than the chamber 52a of FIGS. 14-16. For example, in one embodiment, the separation channel 86 of the chamber 52b of FIGS. 17-19 has a width of approximately 0.2 cm at the top end 80 and a width of approximately 0.35 cm at the bottom end 82, whereas the channel 86 of the chamber 52a of FIGS. 14-16 has a width of approximately 0.4 cm at the top end 80 and a width of approximately 0.57 cm at the bottom end 82. It is contemplated that the width of the top end 80 of the separation channel 86 at the upstream end 90 could be further decreased, though doing so may present manufacturing challenges without improving fluid separation. Due to the relatively small fluid gap, it is practicable for the entire low-G wall 76a of the chamber 52b of FIGS. 17-19 to having a radius that decreases from the upstream end 90 of the separation channel 86 to the downstream end 94 at each axial position, as the chamber volume does not come undesirably large. Limiting the volume of the separation channel 86 is particularly important when the available volume of fluid to be separated is limited (e.g., when only one unit of blood is available to be separated), as less fluid is required to fill the channel 86. A smaller volume also makes it easier to prime the separation channel 86 at the beginning of a procedure and to flush the channel 86 at the end of (or even during) a procedure.

The exact configuration of the low-G wall 76a of the chamber 52b of FIGS. 17-19 may vary without departing from the scope of the present disclosure. In one exemplary embodiment, the radius of the low-G wall 76a at each axial position decreases gradually and uniformly from the upstream end 90 of the separation channel 86 to the downstream end 94. In this case, the low-G wall 76a may be understood as having the shape of a uniform or Archimedean spiral at each axial position. As noted above, in one particular embodiment (when the chamber 52b is configured to be compatible with the centrifuge drive mechanism of the ALYX® processing device), the top end of the low-G wall 76a may uniformly spiral from a maximum radius of 3.8 cm at the upstream end 90 of the separation channel 86 to a minimum radius of 3.65 cm at the downstream end 94 of the channel 86. Other pitches or offsets may be employed, with the preferred pitch or offset depending on the relative importance placed on the degree of cell settling (which is improved by a larger pitch or offset) vs. the total volume of the separation channel 86 (which is reduced by a smaller pitch or offset). While a uniform spiral may be advantageous for the shape of the low-G wall 76a (to encourage uniform flow along the low-G wall 76a), it should be understood that the shape of the low-G wall 76a may follow a different path, such as the path of a non-uniform spiral.

Similar to the above description of the air drain taper 112 of FIGS. 14-16, on account of the high-G wall 78 having an at least substantially uniform radius at each axial position, the decreasing radius of the low-G wall 76a effectively increases the width of the separation channel 86 from the upstream end 90 to the downstream end 94 at each axial position. As noted above, this is in contrast to spiral-shaped fluid flow paths (e.g., ones of the type described in U.S. Pat. No. 9,327,296) in which a low-G wall and a high-G wall both follow a spiral path (resulting in a uniform channel width at each axial position) and known fluid separation chambers in which the width of a separation channel decreases from the upstream end to the downstream end at each axial position. Increasing the width of the separation channel 86 from the upstream end 90 of the channel 86 to the downstream end 94 at each axial position results in a maximum channel width at the downstream end 94. In the case of blood separation, this creates more space for the buffy coat/interface INT to build up at the downstream end 94 of the separation channel 86 and increases the distance between the buffy coat interface INT and the low-G outlet port 96a. While a similar result could conceivably be achieved by providing the separation channel with a greater, uniform width along its entire length (or even by providing a separation channel having a width that increases from the upstream end to the downstream end, but starting from a greater initial width at the upstream end), the configuration of FIGS. 17-19 achieves this result without unnecessarily increasing the total volume of the separation channel 86.

Figure 20:
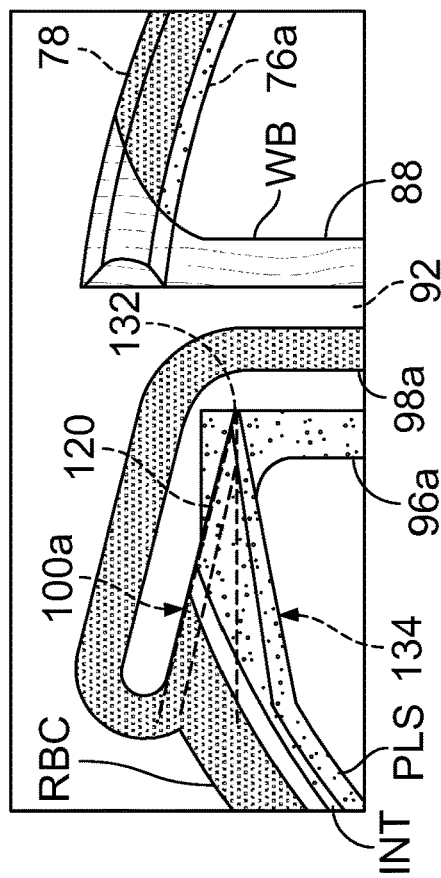
FIG. 20 is a detail view of a bottom end of a ramp of the fluid processing chamber defining the fluid flow path shown in FIGS. 17 and 18.
Figure 21:
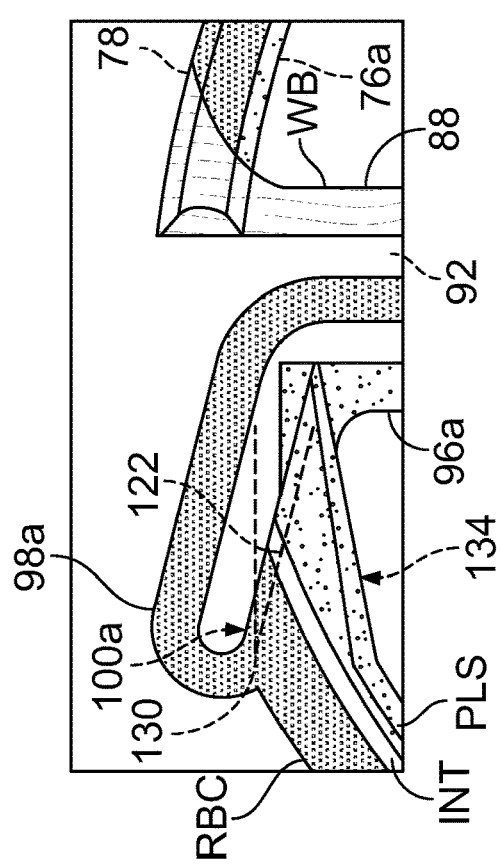
FIG. 21 is a detail view of a top end of the ramp of the fluid processing chamber defining the fluid flow path shown in FIGS. 17 and 18.
Figure 22:
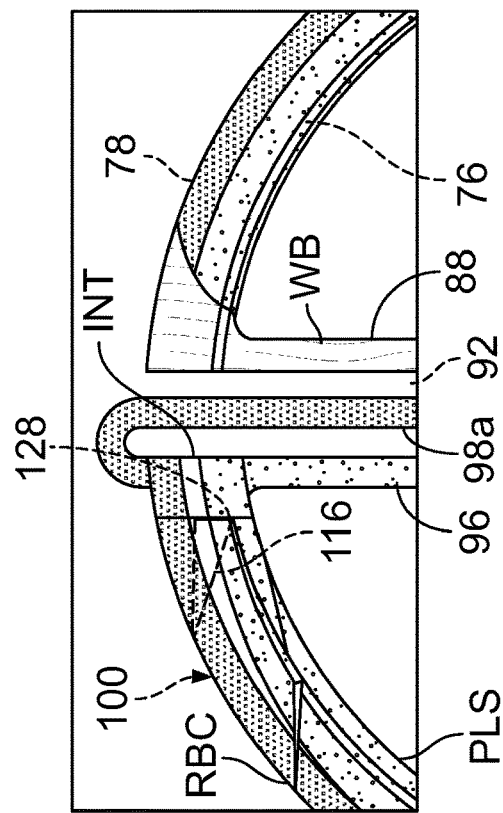
FIG. 22 is a detail view of a bottom end of a ramp of the fluid processing chamber defining the fluid flow path shown in FIGS. 14 and 15.
Figure 23:
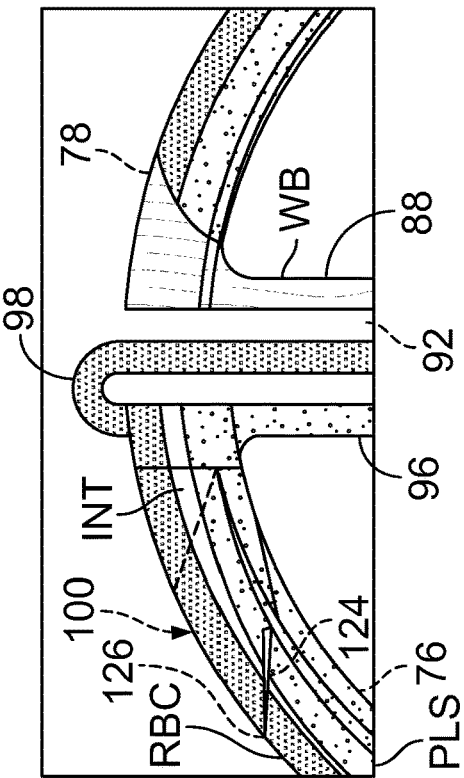
FIG. 23 is a detail view of a top end of the ramp of the fluid processing chamber defining the fluid flow path shown in FIGS. 14 and 15.

Another difference between the embodiment of FIGS. 14-16 and the embodiment of FIGS. 17-19 is the configuration of the ramp, which may be understood with reference to FIGS. 20-25. FIG. 20 highlights the configuration of the bottom end 120 of the ramp 100a of FIGS. 17-19, while FIG. 22 highlights the configuration of the bottom end 116 of the ramp 100 of FIGS. 14-16, FIG. 21 highlights the configuration of the top end 122 of the ramp 100a of FIGS. 17-19, while FIG. 23 highlights the configuration of the top end 124 of the ramp 100 of FIGS. 14-16. The top and bottom ends 122 and 120 of the ramp 100a of FIGS. 17-19 are shown together in FIG. 24, with the top and bottom ends 124 and 116 of the ramp 100 of FIGS. 14-16 being shown together in FIG. 25.

In the embodiment of FIGS. 14-16, the ramp 100 is positioned at the downstream end 94 of the separation channel 86, extending diagonally from a first position 126 of the high-G wall 78 (which position may be referred to as the "upstream end" of the ramp 100) to a second position 128 (downstream of the first position 126) of the low-G wall 76 (which position may be referred to as the "downstream end" of the ramp 100). The outlet passages 96 and 98 open into the separation channel 86 at the downstream end 126 of the ramp 100 (at the bottom end 82 of the channel 86), with the bottom end 116 of the ramp 100 being spaced away from (i.e., positioned above) the bottom end 82 of the channel 86. As described above, the cell settling well 114 provides a flow path in the space between the bottom end 116 of the ramp 100 and the bottom end 82 of the separation channel 86.

As in the embodiment of FIGS. 14-16, the ramp 100a of FIGS. 17-19 is positioned at the downstream end 94 of the separation channel 86, extending diagonally from a first position 130 of the high-G wall 78 (which position may be referred to as the "upstream end" of the ramp 100a) to a second position 132 (downstream of the first position 130) of the low-G wall 76 (which position may be referred to as the "downstream end" of the ramp 100a). However, as can be seen by comparing FIG. 20 to FIG. 22, the downstream end 132 of the ramp 100a of FIGS. 17-19 is positioned much farther downstream than the downstream end 128 of the ramp 100 of FIGS. 14-16. Accordingly, the ramp 100a of FIGS. 17-19 has a greater length (along the circumference of the separation channel 86) than the ramp 100 of FIGS. 14-16. In an exemplary embodiment (in which the chambers 52a and 52b are configured to be compatible with the centrifuge drive mechanism of the ALYX® processing device), the bottom end 116 of the ramp 100 of FIGS. 14-16 has a length of approximately 0.87 cm, whereas the bottom end 120 of the ramp 100a of FIGS. 17-19 has a length of approximately 1.43 cm. In such an embodiment, the top end 124 of the ramp 100 of FIGS. 14-16 has a length of approximately 0.65 cm, whereas the top end 122 of the ramp 100a of FIGS. 17-19 has a length of approximately 1.06 cm. As explained above, the bottom end 82 of the separation channel 86 may have a greater width than the top end 80 of the channel 86 (due to manufacturing considerations), which is why the bottom end of each ramp may have a greater length than the top end of that ramp.

Figure 24:
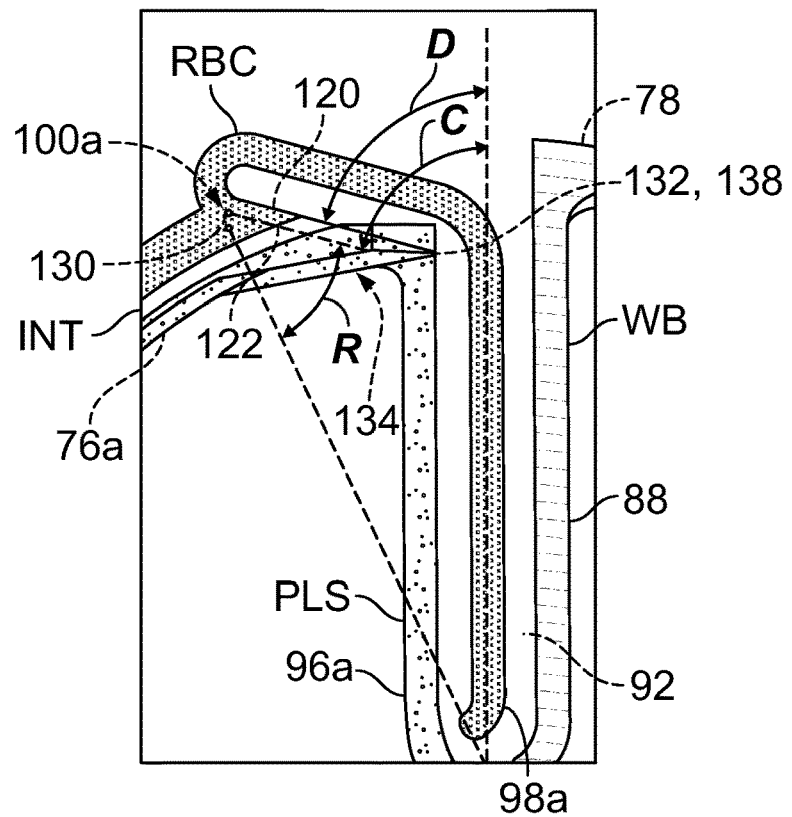
FIG. 24 is a detail view illustrating the orientation of the ramp of the fluid processing chamber defining the fluid flow path shown in FIGS. 17 and 18.

In addition to the ramp 100a of FIGS. 17-19 being longer than the ramp 100 of FIGS. 14-16, the ramp 100a of FIGS. 17-19 also extends across the separation channel 86 at a shallower angle. In the above-described exemplary embodiment, the top end 124 of the ramp 100 of FIGS. 14-16 extends across the separation channel 86 at an angle "T" of approximately 48.85° (relative to a radial line from the central axis of the chamber 52a to the upstream end of the top end 124), with the bottom end 116 of the ramp 100 extending across the channel 86 at an angle "B" of approximately 48.21° (relative to a radial line from the central axis of the chamber 52a to the upstream end of the bottom end 116), as shown in FIG. 25. In such an exemplary embodiment, both the top and bottom ends 122 and 120 of the ramp 100a of FIGS. 17-19 extend across the separation channel 86 at an angle "R" of approximately 50.43° (relative to a radial line from the central axis of the chamber 52b to the upstream end of the ramp 100a), as shown in FIG. 24.

In general, a shallower angle (i.e., a greater angle relative to a radial line from the central axis of the chamber to the upstream end of the ramp) will allow for a longer ramp, and the shallower angle of the ramp 100a of FIGS. 17-19 does allow for an increased length. However, it will be seen that the angles T and B of the ramp 100 of FIGS. 14-16 are similar to the angle R of the ramp 100a of FIGS. 17-19, such that the difference in ramp angle does not entirely account for the difference in lengths of the ramps 100 and 100a. Indeed, the chamber 52b of FIGS. 17-19 defines an additional feature 134 (referred to herein as a "low-G recess feature") that creates more space for the ramp 100a to have a greater length.

Similar to the cell settling well 114 of the chamber 52a of FIGS. 14-16, the low-G recess feature 134 is defined by the chamber 52b of FIGS. 17-19 at the downstream end 94 of the separation channel 86. The low-G recess feature 134 is essentially a generally planar, radially inward departure or extension of the low-G wall 76a from its standard radius (similar to the cell settling well 114 of FIGS. 14-16), extending from a first end 136 to a downstream second end 138 at which the low-G wall 76a has a smaller radius. However, rather than being providing a flow path beneath the ramp 100a (like the cell settling well 114), the low-G recess feature 134 is instead positioned radially inwardly of the ramp 100a, with a portion of the low-G recess feature 134 extending along the entire height of the separation channel 86. In the illustrated embodiment, the entirety of the low-G recess feature 134 extends along the entire height of the separation channel 86, except at its second end 138, where a bottom end 140 of the low-G recess feature 134 is spaced a small distance from (above) the bottom end 82 of the separation channel 86 (FIG. 19). This small gap or space between the bottom end 140 of the low-G recess feature 134 and the bottom end 82 of the separation channel 86 allows fluid flow beneath the second end 138 of the low-G recess feature 134, to the low-G outlet passage 96a. As can be seen in FIG. 24, the second end 138 of the low-G recess feature 134 may coincide with the downstream end 132 of the ramp 100a, with the position of the second end 138 of the low-G recess feature 134 (which is positioned at an especially small radial position) being primarily responsible for the increased length of the ramp 100a.

As described above, the controller of a processing device 10 may determine the position of the interface INT within the separation channel 86 by assessing the pulse width of a signal from the light detector 32 of an optical system. It should be clear that, by providing a longer ramp that extends across the separation channel 86 at a shallower angle (as in the embodiment of FIGS. 17-19), a wider pulse width will be produced at any given position of the interface INT, which may be advantageous for certain interface position control circumstances. Additionally, having the ramp 100a closer to the low-G outlet passage 96a allows for the position of the interface INT to be monitored closer to the low-G outlet passage 96a, which may be advantageous for separation quality. For example, in the case of blood separation, because the buffy coat builds up on the ramp 100a, it may form an inconsistent interface INT, in which case measuring the interface position closer to the low-G outlet passage 96a helps to ensure that the interface INT is maintained at a position sufficiently far from the low-G outlet passage 96a to allow for clean plasma collection.

Another difference between the ramp 100 of FIGS. 14-16 and the ramp 100a of FIGS. 17-19 is that the top and bottom ends 122 and 120 of the ramp 100a of FIGS. 17-19 are positioned at the same approximate circumferential position (as shown in FIG. 24), whereas the top and bottom ends 124 and 116 of the ramp 100 of FIGS. 14-16 are positioned at much different circumferential positions (as shown in FIG. 25). In the embodiment illustrated in FIG. 24, the top end 122 of the ramp 100a is oriented at an angle "C" of approximately 76.04° from a "12:00" position of the chamber 52b, while the bottom end 120 is oriented at an angle "D" of approximately 75.61° from the "12:00" position. In contrast, in the embodiment illustrated in FIG. 25, the top end 124 of the ramp 100 is oriented at an angle "E" of approximately 86.03° from the "12:00" position of the chamber 52a, while the bottom end 116 is oriented at an angle "F" of approximately 70.89° from the "12:00" position. This configuration of the ramp 100 of FIGS. 14-16 arises from maintaining the same approximate angle at all points from the top end 124 of the ramp 100 to the bottom end 116 of the ramp 100 with respect to a radial line extending from the central axis of the chamber 52a.

Yet another difference between the ramp 100 of FIGS. 14-16 and the ramp 100a of FIGS. 17-19 is the position of the high-G outlet passage with respect to the ramp. In the embodiment of FIGS. 14-16, the high-G outlet passage 98 (along with the low-G outlet passage 96) opens into the separation channel 86 downstream of the ramp 100. On the other hand, in the embodiment of FIGS. 17-19, the high-G outlet passage 98a opens into the separation channel 86 at the upstream end 130 of the ramp 100a (FIG. 21), with the high-G outlet passage 98a extending radially outwardly and then downstream and past the downstream end 132 of the ramp 100a. Such a configuration provides additional space between the positions at which the two outlet passages 96a and 98a open into the separation channel 86, which is advantageous in reducing the risk that turbulence at the opening of either outlet passage affects fluid flow to the other outlet passage.

One final difference between the chamber of FIGS. 14-16 and the chamber of FIGS. 17-19 is that the chamber of FIGS. 17-19 defines a second feature 142 (in addition to the low-G recess feature 134) configured to improve the purity of the plasma layer PLS exiting the separation channel 86 via the low-G outlet passage 96a. Similar to the low-G recess feature 134, this second feature 142 (which may be referred to as a "fluid velocity reduction feature") is defined by the chamber at the downstream end 94 of the separation channel 86, adjacent to the ramp 100a. However, whereas the low-G recess feature 134 is positioned radially inwardly of the ramp 100a, the fluid velocity reduction feature 142 is instead positioned beneath a portion of the ramp 100a, similar to the cell settling well 114 of FIGS. 14-16. More particularly, the fluid velocity reduction feature 142 is a fluid flow path (which may be generally block-shaped, in an exemplary embodiment) defined by the chamber in the space between the bottom end 120 of the ramp 100a and the bottom end 82a of the separation channel 86.

The fluid velocity reduction feature 142 is, thus, similar to the cell settling well 114 in that it allows for fluid flow in the space between the ramp 100a and the bottom end 82 of the separation channel 86. However, the fluid velocity reduction feature 142 is different from the cell settling well 114 in the degree of fluid flow that is allowed. In particular, whereas the bottom end 116 of the ramp 100 of FIGS. 14-16 is entirely spaced from the bottom end 82 of the separation channel 86 (such that the cell settling well 114 provides a fluid flow path beneath the entire ramp 100), only a portion of the ramp 100a of FIGS. 17-19 is spaced from the bottom end 82 of the channel 86. Additionally, as in the illustrated embodiment, a radially outer surface 144 of the fluid velocity feature 142 may be defined by a generally planar extension at the bottom of the ramp 100a (FIG. 19), which further limits the thickness of a separated fluid component that may flow through the fluid velocity feature 142. Thus, the fluid velocity reduction feature 142 provides a narrower fluid flow path, allowing less fluid flow than the cell settling well 114. Indeed, as best shown in FIG. 19, the fluid velocity reduction feature 142 may be configured to allow only the plasma layer PLS to flow beneath the ramp 100a (to reach the low-G outlet passage 96a), whereas the cell settling well 114 allows for all of the separated fluid components to flow beneath the ramp 100 (to reach the two outlet passages 96 and 98).

If the entire bottom end 120 of the ramp 100a extended to the bottom end 82 of the separation channel 86 (i.e., if the fluid velocity reduction feature 142 were not provided), the region of the channel 86 directly adjacent to the opening of the low-G outlet passage 96a (which comprises the flow path defined beneath the second end 138 of the low-G recess feature 134) would be relatively constricted, increasing the flow rate of fluid through that region. This hypothetical constricted region is illustrated in FIG. 19 as the portion of the channel 86 to the left of line "V". By providing the fluid velocity reduction feature 142, the width of the region of the channel 86 directly adjacent to the opening of the low-G outlet passage 96a is thus increased (to encompass the regions to the left and right of line V), reducing the flow rate of fluid through that region and reducing the likelihood of a substance from the interface INT (e.g., platelets, in the case of blood separation) reaching the low-G outlet passage 96a. It should be understood that, while the fluid velocity reduction feature 142 is shown in combination with the low-G recess feature 134 (which combination of features improves the purity of the plasma layer PLS exiting the separation channel 86 via the low-G outlet passage 96a), the two features may be provided separately.

FIGS. 26 and 27 illustrate a chamber 52c that is similar to the one of FIGS. 17-19, with the one distinction being the position at which the inlet passage 88a opens into the separation channel 86. In the embodiments of FIGS. 14-16 and 17-19, the inlet passage 88 opens into the separation channel 86 at the upstream end 90 of the channel 86 and at the bottom end 82 of the channel 86. However, in the embodiment of FIGS. 26 and 27, the inlet passage 88a (while still opening into the separation channel 86 at the upstream end 90) opens into the channel 86 at the top end 80 of the channel 86. It has been found that, in some separation circumstances, when the fluid both enters the separation channel 86 and exits the channel 86 at the bottom end 82 of the channel 86, the fluid and separated fluid components may favor the bottom half of the channel 86 because the convection pathway within the fluid path is located along the bottom end 82 of the channel 86 (i.e., there is no flow present to push the fluid or fluid components toward the top half of the channel 86). Reconfiguring the inlet passage 88a to open into the separation channel 86 at the top end 80 of the channel 86 creates a convective flow pathway from the top end 80 of the channel 86 (at the inlet passage 88a) to the bottom end 82 of the channel 86 (at the outlet passages 96a and 98a). This enables more of the surface area of the low- and high-G walls 76a and 78 to be used for separation which, in the case of blood separation may lead to higher achievable hematocrit for the separated red blood cells and improved sedimentation of the platelets into the buffy coat/interface INT.

FIGS. 28-33 illustrate another exemplary fluid separation chamber 52d embodying aspects of the present disclosure. The chamber 52d of FIGS. 28-33 is similar in some respects to the previously described fluid separation chambers and different in other respects. As in the previously described fluid separation chambers, the chamber 52d includes a central hub 74 coinciding with a rotational axis, with a plurality of radial walls extending from the central hub 74 to a single-stage separation channel 86 defined between a generally annular low-G wall 76b and a generally annular high-G wall 78a. Also similar to the previously described chambers, the radial walls of the chamber 52d define a terminal wall 92 separating an upstream end 90 of the separation channel 86 from a downstream end 94.

The low-G wall 76b of the chamber 52d has a radius that decreases at each axial position from a maximum radius at the upstream end 90 of the separation channel 86 to a minimum radius at the downstream end 94, similar to the chamber 52b of FIGS. 17-19. However, in the embodiment of FIGS. 28-33, the high-G wall 78a also has a radius that decreases at each axial position from a maximum radius at the upstream end 90 of the separation channel 86 to a minimum radius at the downstream end 94. The curvatures of the low-G wall 76b and the high-G wall 78a may differ, in which case the width of the separation channel 86 may vary from the upstream end 90 to the downstream end 94. Alternatively, and as shown in the illustrated embodiment, the low-G wall 76b and the high-G wall 78a may have similar curvatures, with the width of the separation channel 86 remaining uniform (or at least substantially uniform) from the upstream end 90 of the channel 86 to the downstream end 94 of the channel 86 at each axial position.

While the exact configurations of the low-G and high-G walls 76b and 78a of the chamber 52d of FIGS. 28-33 may vary, it may be advantageous to maximize the surface area of the high-G wall 78a because it is the separation surface area for the RBC layer RBC, such that maximizing the surface area of the high-G wall 78a will maximize the separation surface area for the RBC layer RBC. In the case of blood separation, maximizing the separation surface area for the RBC layer RBC will maximize the achievable hematocrit of the red blood cell product at a particular centrifuge rotation rate. The surface area of the high-G wall 78a is a function of the radius and height of the high-G wall 78a, along with the curvature of the high-G wall 78a from the upstream end 90 of the separation channel 86 to the downstream end 94. In one particular embodiment (which is suitable for use in combination with the centrifuge drive mechanism of the ALYX® processing device), at its upstream end 90, the separation channel 86 has a height of approximately 6.1 cm, with a high-G wall radius of approximately 4.1 cm at the bottom end 82 and 4.0 cm at the top end 80 (on account of the above-described 1° taper away from the central axis of the chamber 52d, from the top end 80 to the bottom end 82). The surface area of such a high-G wall 78a may be approximately 141.6 cm², which may be near the maximum possible for a chamber 52d configured to be compatible with the centrifuge drive mechanism of the ALYX® processing device.

As for the low-G wall 76b, in the above-described exemplary embodiment (in which the high-G wall 78a has a radius of approximately 4.1 cm at the bottom end 82 and 4.0 cm at the top end 80), at the upstream end 90 of the separation channel 86, it may have a radius of approximately 3.6 cm at the bottom end 82 and 3.7 cm at the top end 80 (on account of the above-described 1° inward taper toward the central axis of the chamber 52d, from the top end 80 to the bottom end 82). The radii of the low-G wall 76b and the high-G wall 78a at any downstream position depends on the particular curvature of the walls 76b and 78a.

Figure 29:
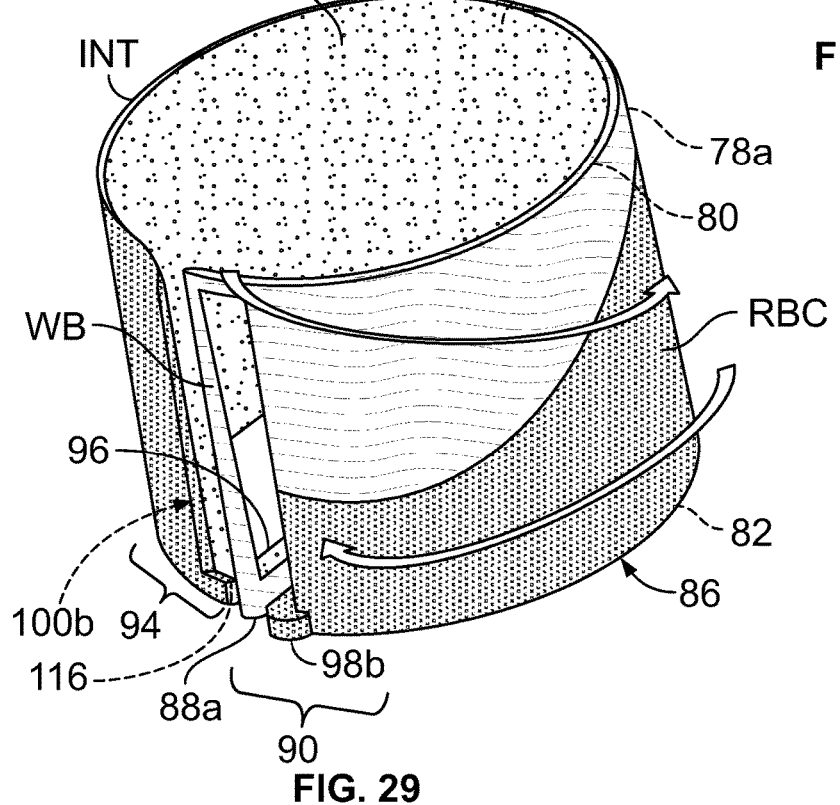
FIG. 29 is a perspective view of the fluid flow path of FIG. 28.
Figure 30:
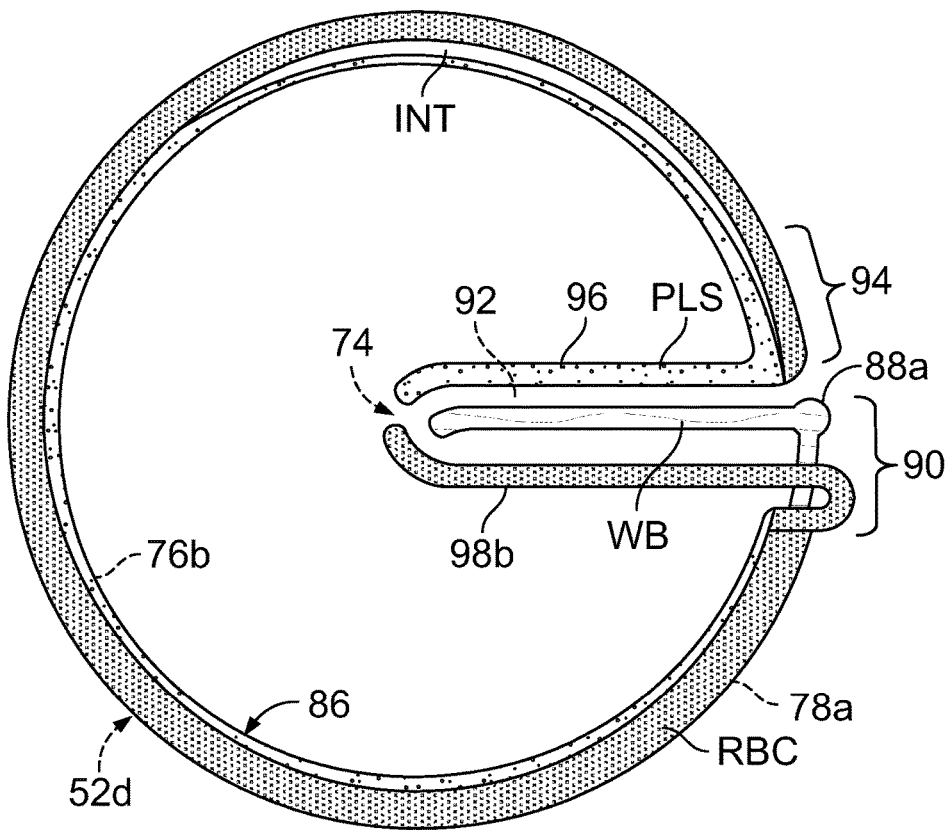
FIG. 30 is a bottom plan view of the fluid flow path of FIG. 28.

In one exemplary embodiment (which is illustrated in FIGS. 28-33), the radius of each of the low-G wall 76b and the high-G wall 78a decreases gradually and uniformly from the upstream end 90 of the separation channel 86 to the downstream end 94 at each axial position. In this case, the low-G wall 76b and the high-G wall 78a (and, thus, the separation channel 86 itself) may be understood as each having the shape of a uniform or Archimedean spiral at each axial position, as best shown in FIG. 30. As also can be seen in FIG. 30, when the chamber 52d is rotated at an appropriate rate, the radial position of the RBC layer RBC remains substantially uniform from the upstream end 90 of the separation channel 86 to the downstream end 94 of the channel 86. If the separation channel 86 had a uniform radius, the thickness of the RBC layer RBC would remain uniform or at least substantially uniform from the upstream end 90 of the channel 86 to the downstream end 94. However, on account of the separation channel 86 having a uniform (or at least substantially uniform) width and a spiral shape (or at least a radius that decreases in some manner from the upstream end 90 of the channel 86 to the downstream end 94), the RBC layer RBC will instead have a greater thickness at the upstream end 90 of the channel 86 than at the downstream end 94, as shown in FIG. 30.

As the thickness of the ABC layer RBC gradually decreases from the upstream end 90 of the separation channel 86 to the downstream end 94, the thickness of the plasma layer PLS will be greater at the downstream end 94 than at the upstream end 90 (also on account of the decreasing radius of the channel 86 from the upstream end 90 to the downstream end 94). If the chamber 52d is rotated at a relatively low rate (which is effective to separate a fluid into two layers), the thickness of the plasma layer PLS will gradually increase from the upstream end 90 of the separation channel 86 to the downstream end 94. However, when the chamber 52d is rotated at a higher rate (which is effective to separate the fluid into three layers), the thickness of the plasma layer PLS may not uniformly increase from the upstream end 90 of the separation channel 86 to the downstream end 94, but may rather increase, before temporarily decreasing and then increasing again (as shown in FIG. 30). This is due to the thickness of the interface INT increasing and then decreasing toward the downstream end 94 of the separation channel 86, with the change in thickness of the interface INT being inversely related to the change in thickness of the plasma layer PLS.

The change in thickness or taper of the plasma layer PLS promotes flow toward the low-G outlet passage 96, which is positioned at the downstream end 94 of the separation channel 86. Indeed, it has been found that providing a separation channel 86 with a spiral shape has a significant benefit of increasing the volume of plasma that may be extracted, which may lead to shorter procedure times. One reason for this is that, at a greater RBC layer RBC thickness (which occurs when the RBC layer RBC has a greater hematocrit, in the case of blood separation), the interface between the separated components will be closer to the low-G wall 76b, particularly at the upstream end 90 of a separation channel 86 having a radius that decreases from its upstream end 90 to its downstream end 94. With an ABC layer ABC having a high hematocrit (in the case of blood separation) and moving in contact with both the low-G wall 76b and the high-G wall 78a, a significant shear rate could be expected. Due to blood being a non-Newtonian shear thinning fluid, its viscosity decreases as shear rate increases, allowing for the ABC layer RBC to have a greater hematocrit which, in turn, allows for greater plasma extraction efficiency, according to the relationship of Stoke's Law as applied to continuous flow separation.

However, while a separation channel 86 having a radius that decreases from its upstream end 90 to its downstream end 94 may enhance plasma separation efficiency, the risk of platelets being pulled from the interface INT into the low-G outlet passage 96 may also increase. One reason for this is due to the separation surface for platelets being the surface of the red blood cell bed. As such, increasing or maximizing the hematocrit of the RBC layer ABC (which makes the ABC layer RBC thicker) will move the red blood cell bed closer to the low-G wall 76b, which decreases the separation surface area for platelets (due to the decreased radius of the red blood cell bed).

Thus, it should be clear that a significant factor in the preferred configuration of the separation channel 86 (including the manner and degree in which its radius decreases from its upstream end 90 to its downstream end 94) will be whether plasma purity or separation efficiency is prioritized. In general, when plasma purity is prioritized, it may be advantageous to employ a smaller or more gentle spiral (i.e., one resulting in a smaller difference between the radii of the separation channel 86 at the upstream and downstream ends 90 and 94). On the other hand, when it is desired to maximize plasma extraction efficiency, a larger spiral (i.e., one resulting in a greater difference between the radii of the separation channel 86 at the upstream and downstream ends 90 and 94 of the channel 86) may be advantageous. Additionally, a larger spiral will tend to allow air to more readily exit the separation channel 86 via the low-G outlet passage 96 during priming, such that a larger spiral may be preferred when air removal is a higher priority. Furthermore, it has been found that a reduced separation surface area for platelets will lead to fewer platelet sedimentation issues when processing smaller amounts of blood, such that a larger spiral may be more suitable for processing a single unit of blood, rather than an apheresis setting in which a much greater volume of blood is to be processed.

In addition to a separation channel 86 having a radius that decreases from its upstream end 90 to its downstream end 94, the chamber 52d of FIGS. 28-33 also differs from the embodiments of FIGS. 5-27 with regard to the location of the high-G outlet passage 98b. In the chambers of FIGS. 5-27, the high-G outlet passage opens into the separation channel at the downstream end of the channel, whereas the high-G outlet 98b of the chamber 52d of FIGS. 28-33 opens into the channel 86 at the upstream end 90. Although the chamber 52d of FIGS. 28-33 is shown with a spiral-shaped separation channel 86 and a high-G outlet passage 98b that opens into the channel 86 at the upstream end 90 it should be understood that these features may be practiced separately.

The inlet passage 88a also opens into the separation channel 86 at the upstream end 90, so care must be taken to ensure that fluid entering the channel 86 via the inlet passage 88a does not flow directly into the high-G outlet passage 98b without separating. In the illustrated embodiment, this direct flow from the inlet passage 88a to the high-G outlet passage 98b is avoided by configuring the inlet passage 88a to open into the separation channel 86 at the top end 80 of the channel 86, while the high-G outlet passage 98b opens into the channel 86 at the bottom end 82. FIG. 29 shows the general direction of flow of the RBC layer RBC from the time it enters the separation channel 86 (as part of an unseparated fluid) via the inlet passage 88a to the time it exits the channel 86 via the high-G outlet passage 98b. As can be seen in FIG. 29, fluid enters the upstream end 90 of the separation channel 86 via the inlet passage 88a and begins to move toward the low-G outlet passage 96 at the downstream end 94 of the channel 86. The fluid separates into two or more component parts as it moves through the separation channel 86, with the RBC layer RBC reversing direction at some point within the channel 86 and moving in a general direction from the downstream end 94 of the channel 86 toward the upstream end 90. FIGS. 28-33 show at least a portion of the RBC layer RBC moving to the downstream end 94 of the separation channel 86 before reversing direction, but it should be understood that the RBC layer RBC may not necessarily reach the downstream end 94 of the channel 86 before reversing direction.

In the case of blood separation, this reverse movement of the RBC layer RBC has been found to pull platelets and the buffy coat/interface INT away from the low-G outlet passage 96, producing a more pure (platelet-poor) plasma product, while also increasing buffy coat/interface INT collection efficiency. Additionally, it has been found that causing the RBC layer RBC to reverse direction (rather than moving along the entire high-G wall 78a from the upstream end 90 of the separation channel 86 to the downstream end 94) does not result in an unacceptable decrease in the hematocrit of the RBC layer RBC or in plasma extraction efficiency. This is especially true when the separation channel 86 also has a decreasing radius or spiral shape, as in the illustrated embodiment.

Figure 31:
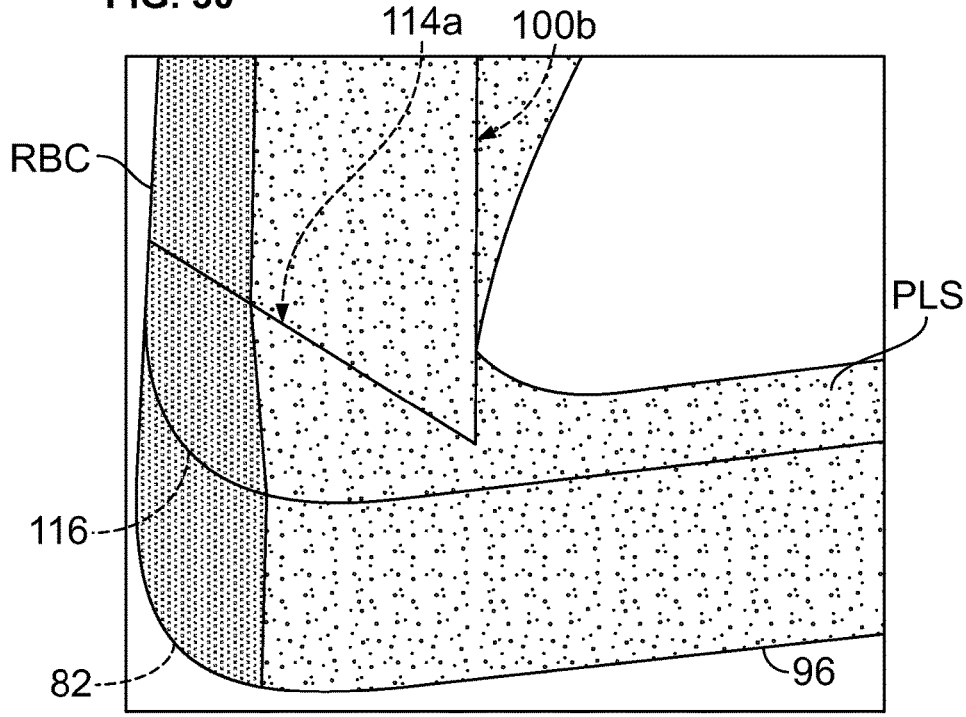
FIG. 31 is a detail view of a downstream end of the fluid flow path of FIG. 28.
Figure 32:
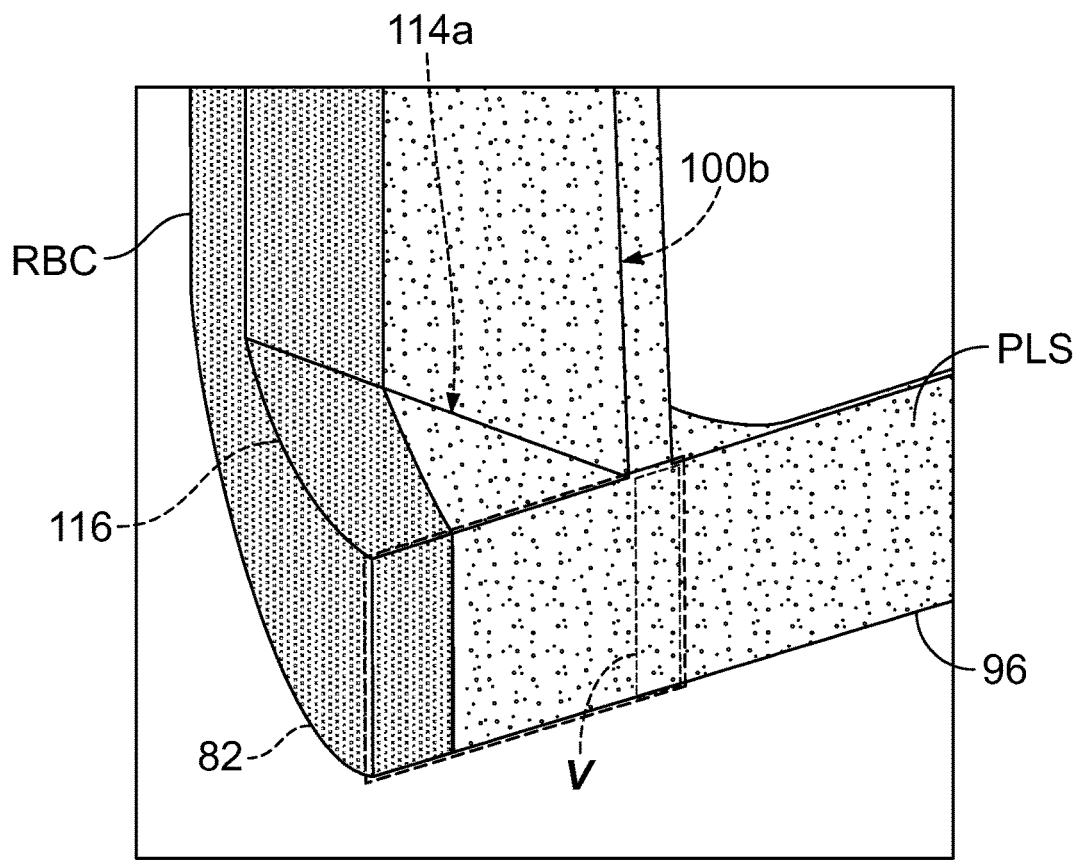
FIG. 32 is a cross-sectional view of the downstream end of the fluid flow path shown in FIG. 31.
Figure 33:
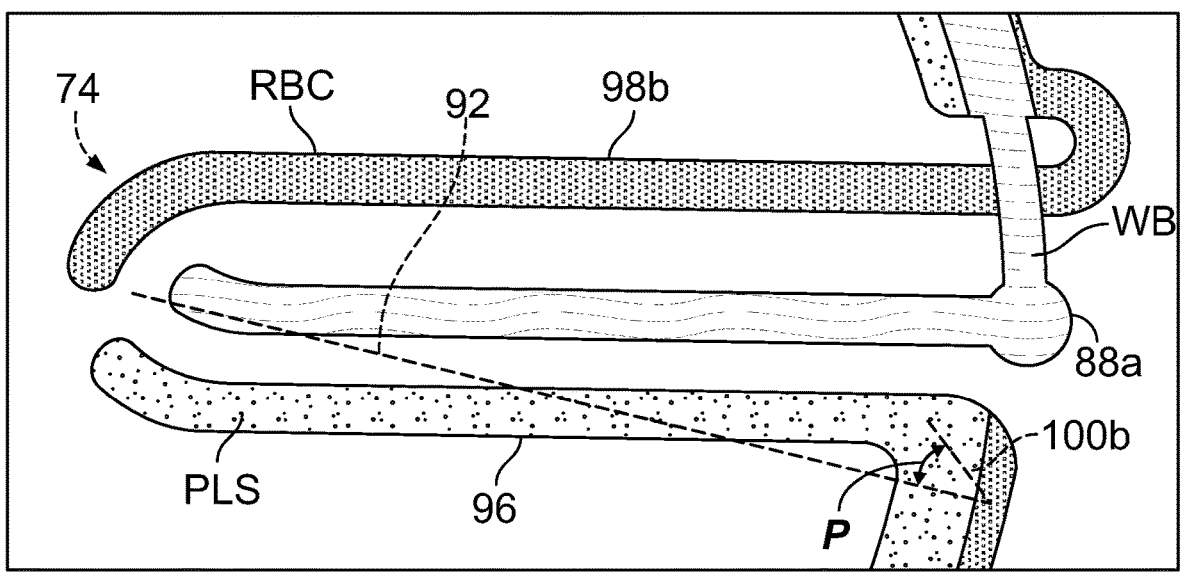
FIG. 33 is a detail view of a top end of the ramp of the fluid processing chamber defining the fluid flow path shown in FIG. 28.
Figure 35:
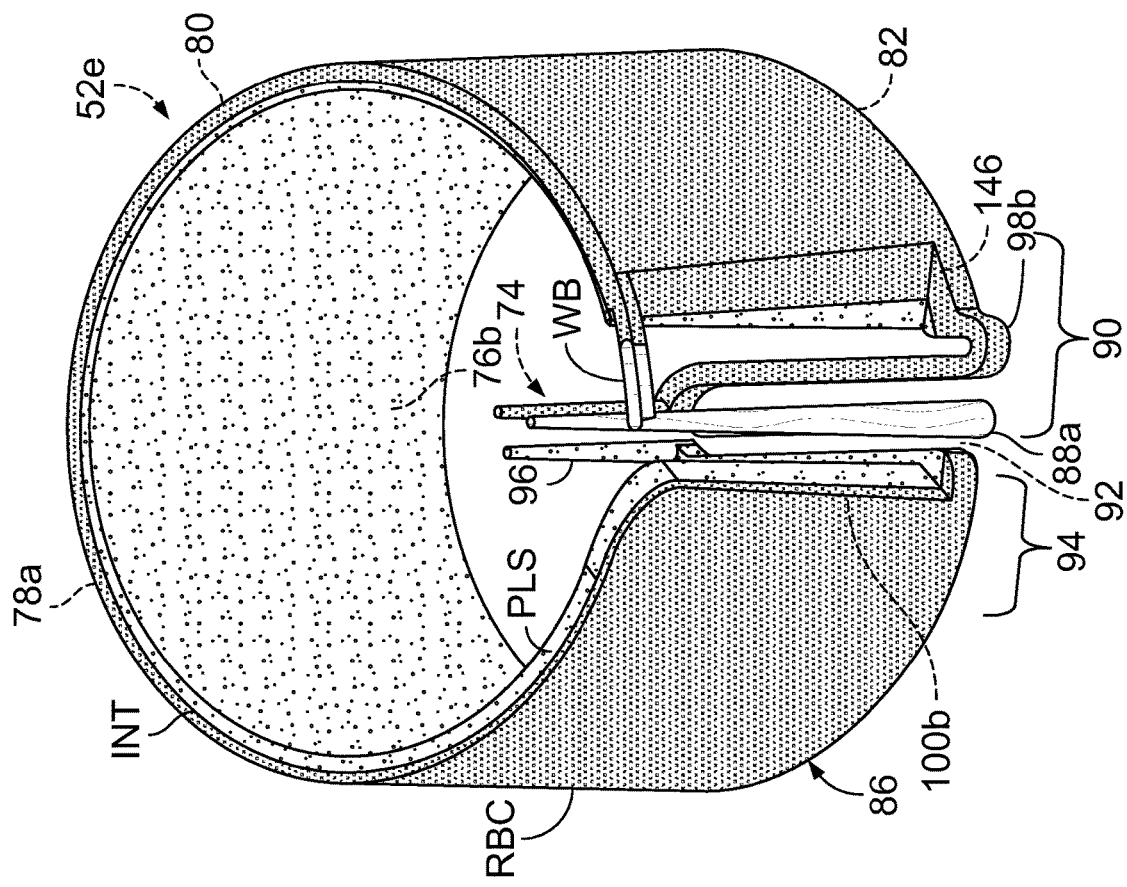
FIG. 35 is a perspective view of fluid flow through the fluid processing chamber of FIG. 34.
Figure 34:
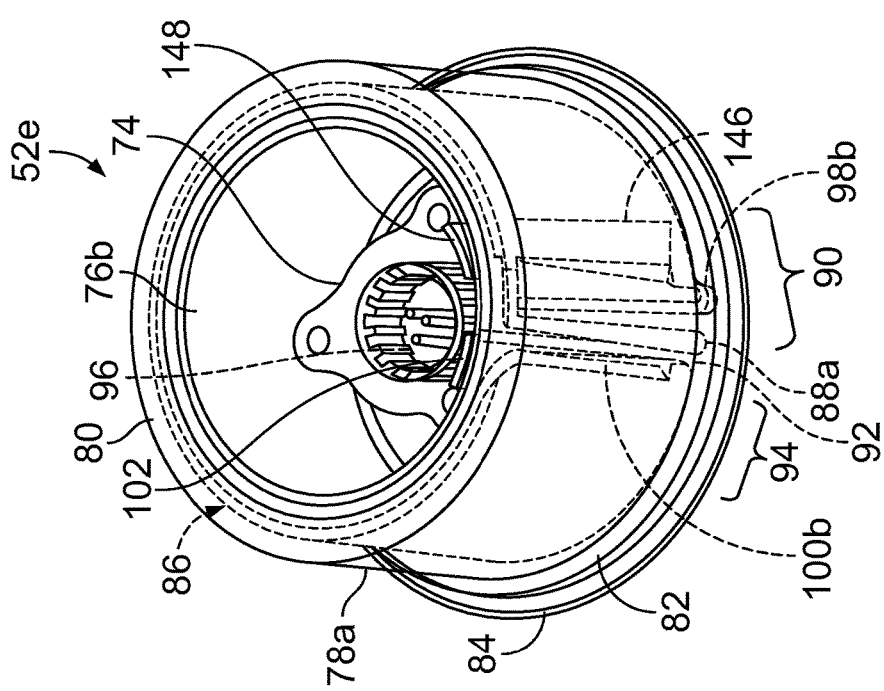
FIG. 34 is a perspective view of another exemplary embodiment of a fluid processing chamber according to an aspect of the present disclosure, showing fluid flow through the chamber.

In addition to a spiral-shaped separation channel 86 and a high-G outlet passage 98b positioned at the upstream end 90 of the channel 86, the chamber 52d of FIGS. 28-33 may also include a ramp 100b. In the illustrated embodiment, the ramp 100b is oriented at a 45° angle "P" with respect to the radius line of the high-G wall 78a (as shown in FIG. 33), with a bottom end 116 that is entirely spaced from the bottom end 82 of the separation channel 86. However, it should be understood that other ramp orientations and configurations may be employed, with the consequences of different ramp orientations and configurations being described above in greater detail.

On account of the bottom end 116 of the illustrated ramp 100b being spaced away from the bottom end 82 of the separation channel 86, a gap is defined between the bottom end 116 of the ramp 100b and the bottom end 82 of the separation channel 86. A cell settling well 114a (FIGS. 31 and 32) allows for fluid flow through the gap to further improve the purity of the plasma layer PLS exiting the separation channel 86 via the low-G outlet passage 96. In particular, the cell settling well 114a increases the channel area available for flow near the low-G outlet passage 96, thereby reducing the fluid velocity in the vicinity of the low-G outlet passage 96, which reduces the likelihood of platelets being pulled into the low-G outlet passage 96 (in the case of blood separation). Similar to FIG. 19, FIG. 32 shows the additional flow area provided by the cell settling well 114a (as represented by the portion of the channel 86 to the left of line "V"), which maintains the consistent high-G to low-G fluid thickness of the separation channel 86 in the vicinity of the low-G outlet passage 96 to prevent an increase in flow rate.

While the formation 114a allowing for fluid flow through the gap between the bottom end 116 of the ramp 100b and the bottom end 82 of the separation channel 86 is referred to herein as a "cell settling well," it will be seen that it has similarities to both the cell settling well 114 of the chamber 52a of FIGS. 14-16 and the fluid velocity reduction feature 142 of the chamber 52b of FIGS. 17-19 (such that it could alternatively be referred to as a "fluid velocity reduction feature" or something else entirely). In particular, the cell settling well 114a of FIGS. 31 and 32 is similar to the cell settling well 114 of FIGS. 14-16 to the extent that it defines a fluid flow path beneath the entire bottom end 116 of the ramp 100b (whereas the ramp 100a of FIGS. 17-19 includes a portion extending to the bottom end 82 of the separation channel 86). Such a configuration allows for a greater amount of fluid flow through the cell settling well 114a than through the fluid velocity reduction feature 142. At the same time, the cell settling well 114a of FIGS. 31 and 32 is similar to the fluid velocity reduction feature 142 to the extent that it is relatively short in the axial or vertical direction, whereas the cell settling well 114 of FIGS. 14-16 is taller in the axial or vertical direction (e.g., on the order of one quarter of the height of the separation channel 86). The greater height of the cell settling well 114 of FIGS. 14-16 allows for a greater degree of cell settling, though the fluid velocity reduction feature 142 and the shorter cell settling well 114a may also induce some cell settling.

FIGS. 34-38 illustrate another exemplary fluid separation chamber 52e and the position of various fluid components within a fluid separation channel 86 defined by the fluid separation chamber 52e. The chamber 52e and the fluid separation channel 86 it defines may be understood as a variation of the fluid separation chamber 52d and fluid separation channel 86 of FIGS. 28-33, so the aspects and features of the chamber 52e of FIGS. 34-38 that are common to both chambers 52d and 52e will not be described in detail. Additionally, it should be understood that the techniques illustrated in FIGS. 34-38 and described below may be applied to any of the other fluid separation chambers and channels described herein, along with being applicable to more conventionally configured fluid separation chambers and channels (e.g., those having a ramp positioned at an upstream end of the fluid separation channel).

The most notable difference between the fluid separation chamber 52e of FIGS. 34-38 and the other fluid separation chambers described herein is the inclusion of a ramp 146, which is positioned at the upstream end 90 of the fluid separation channel 86. Thus, the fluid separation chamber 52e and channel 86 of FIGS. 34-38 includes a pair of ramps 100b and 146, with one ramp 100b positioned at the downstream end 94 of the channel 86 (as in the other fluid separation chambers and channels described herein) and one ramp 146 positioned at the upstream end 90 of the channel 86.

Figure 36:
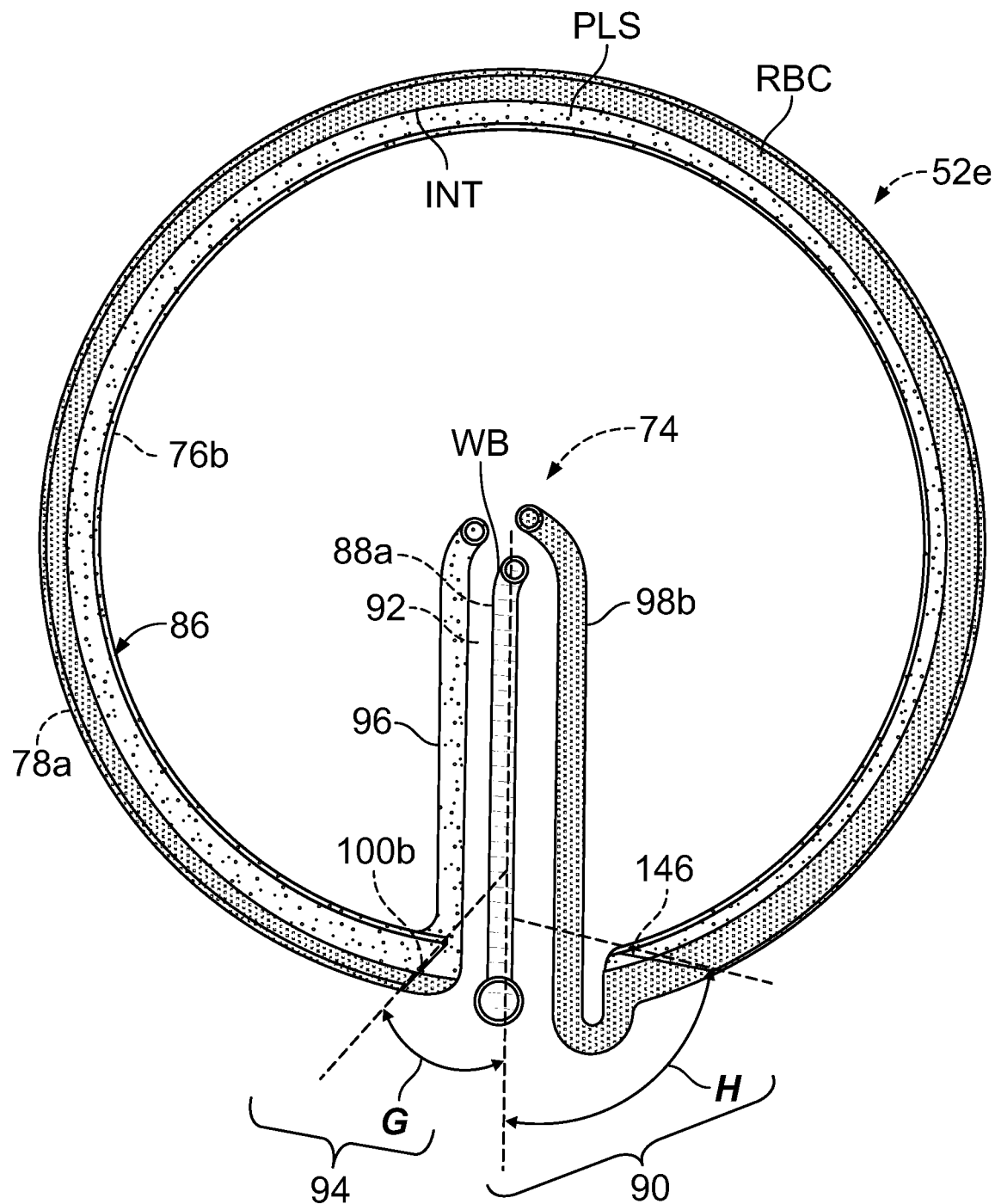
FIG. 36 is a plan view of fluid flow through the fluid processing chamber of FIG. 34.

Similar to the downstream ramps described herein, the upstream ramp 146 extends generally diagonally across the fluid separation channel 86 to make the interface INT between the RBC layer RBC and the plasma layer PLS more discernible for detection through a light-transmissive portion of the chamber 52e. FIG. 36 illustrates exemplary angles G and H at which the downstream ramp 100b and upstream ramp 146 may extend across the fluid separation channel 86. In the illustrated embodiment, the upstream ramp 146 extends across the channel 86 at a shallower angle than the downstream ramp 100b, but it is within the scope of the present disclosure for the downstream ramp 100b to instead extend across the channel 86 at a shallower angle than the upstream ramp 146 or for the ramps 100b and 146 to extend across the channel 86 at the same angle. It will be seen that the orientation of the upstream ramp 146 is generally opposite to the orientation of the downstream ramp 100b, with the downstream ramp 100b extending from the high-G wall 78a toward the low-G wall 76b in the downstream direction, while the upstream ramp 146 extends from the low-G wall 76b toward the high-G wall 78a in the downstream direction.

As described above, a shallower angle will result in a longer ramp, as can be seen in FIG. 36, which shows the upstream ramp 146 as having a greater length than the downstream ramp 100b. Such a configuration may be advantageous when the plasma layer PLS is of most interest, as the steeper angle of the downstream ramp 100a will be more effective to force any platelets on the ramp 100a to slide back toward the interface INT than a shallower angle. The shallower angle of the upstream ramp 146 creates a larger "viewing window" near the high-G outlet passage 98b, where the red blood cells are not yet as packed or compacted as at the downstream end 94. In any event, it should be understood that the particular angle of extension and length of each ramp 100b, 146 may depend on any of a number of factors (e.g., the desired separation and control features) and may vary without departing from the scope of the present disclosure.

Figure 37:
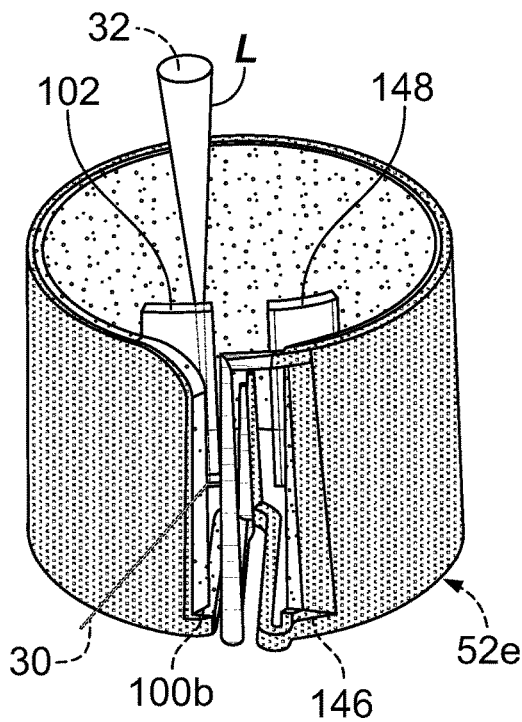
FIG. 37 illustrates optical detection of the radial position of an interface between separated fluid components at a downstream end of a separation channel defined by the fluid processing chamber of FIG. 34.
Figure 37A:
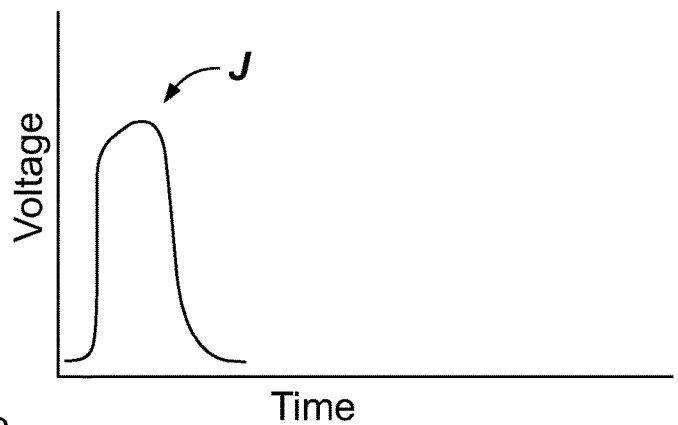
FIG. 37A is a diagrammatic view of the voltage output or signal transmitted by a light detector during detection of the radial position of the interface between separated fluid components at the downstream end of the separation channel defined by the fluid processing chamber of FIG. 34.

As described above, reflectors (each illustrated in FIGS. 34, 37, and 38 as a prismatic reflector 102, 148) are associated with the low-G wall 76b of the chamber 86, angularly aligned with an associated ramp 100b, 146. Thus, as shown in FIG. 37, light L from a light source 30 that passes through the downstream ramp 100b and the fluid components angularly aligned with the ramp 100b within the fluid separation channel 86 will reach the prismatic reflector 102 and be directed to a light detector 32. As described above in greater detail, the pulse width or duration of a signal J transmitted from the light detector 32 to the controller (FIG. 37A) is indicative of the radial position of the interface INT at the downstream end 94 of the channel 86. The upstream ramp 146 and associated prismatic reflector 148 similarly cooperate to transmit light L from the same light source 30 to the same light detector 32 to generate a signal K indicative of the radial position of the interface INT at the upstream end 90 of the channel 86 (FIG. 38A).

Figure 38:
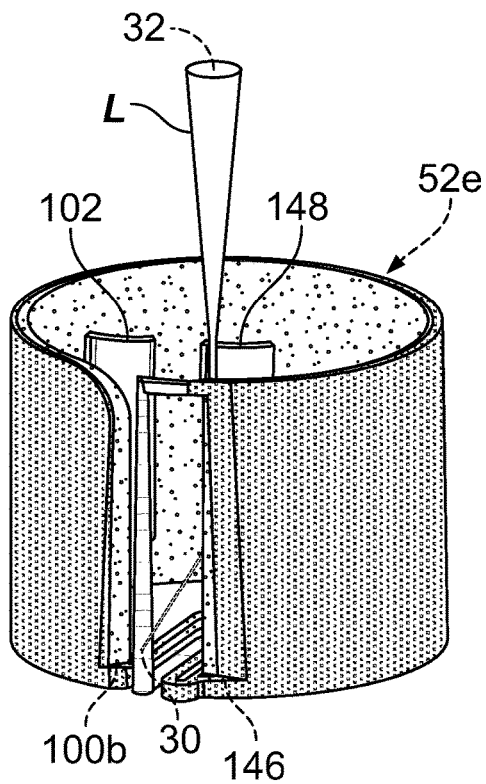
FIG. 38 illustrates optical detection of the radial position of an interface between separated fluid components at an upstream end of the separation channel defined by the fluid processing chamber of FIG. 34.
Figure 38A:
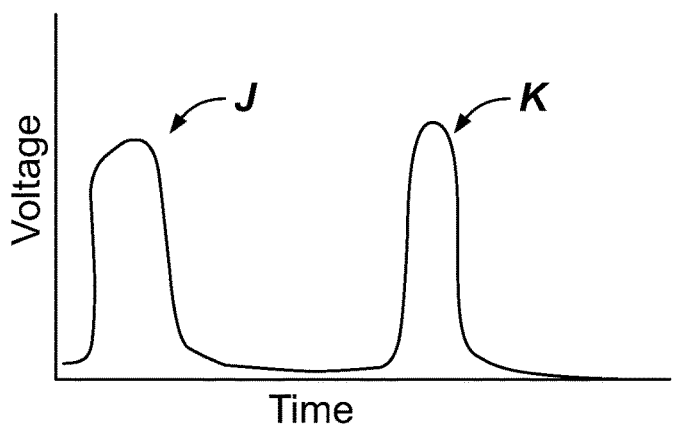
FIG. 38A is a diagrammatic view of the voltage output or signal transmitted by a light detector during detection of the radial position of the interface between separated fluid components at the upstream end of the separation channel defined by the fluid processing chamber of FIG. 34.

FIG. 38A illustrates the signal J indicative of the radial position of the interface INT at the downstream end 94 of the channel 86 being transmitted from the light detector 32 to the controller before the signal K indicative of the radial position of the interface INT at the upstream end 90 of the channel 86, but it should be understood that the order in which the signals J and K are transmitted will depend on the direction of rotation of the fluid separation chamber 52e and may vary without departing from the scope of the present disclosure. It should also be understood that, while the illustrated embodiment employs a pair of prismatic reflectors 102 and 148, it is within the scope of the present disclosure for a single, elongated prismatic reflector to be employed to detect the radial positions of the interface INT at both the downstream and upstream ends of the channel 86, with it also being contemplated that two light source/light detector pairs may be used to detect the radial positions of the interface INT at the downstream and upstream ends of the channel 86, rather than a single light source/light detector pair being used.

As most clearly shown in FIG. 36, the radial position of the interface INT at the downstream end 94 of the fluid separation channel 86 will typically be different from the radial position of the interface INT at the upstream end 90 of the channel 86. Thus, detecting the radial positions of the interface INT at the upstream and downstream ends of the channel 86 is not redundant, but rather provides additional information regarding the position of the interface INT along the length of the channel 86.

With this additional information, different techniques for controlling the position of the interface INT are possible, with a controller being configured to implement one or more of the possible techniques. For example, the controller may compare the radial position of the interface INT at the downstream end 94 of the channel 86 to the expected or target position of the interface INT at the downstream end 94 of the channel 86 to determine whether any aspects of fluid separation require adjustment to properly position the interface INT. Alternatively, the controller may compare the radial position of the interface INT at the upstream end 90 of the channel 86 to the expected or target position of the interface INT at the upstream end 90 of the channel 86 to determine whether any adjustments are required to properly position the interface INT. The controller may alternatively compare some other calculated radial position of the interface INT to a target or expected value to determine whether the position of the interface INT should be changed. For example, the radial position of the interface INT may be calculated as an average of the radial positions of the interface INT at the upstream and downstream ends of the channel 86. This may include the radial positions of the interface INT at the upstream and downstream ends of the channel 86 being either equally or differently weighted when calculating the radial position of the interface INT.

The preferred interface radial position to be compared to an expected or target position may vary depending on any of a number of factors. For example, during a plasma collection procedure, it may be advantageous to compare the radial position of the interface INT at the downstream end 94 of the channel 86 (corresponding to signal J of FIG. 37A) to an expected or target position, as that value is indicative of the radial position of the interface INT adjacent to the low-G outlet passage 96. On the other hand, during a buffy coat collection procedure, it may be advantageous to monitor the radial position of the interface INT at the upstream end 90 of the channel 86 (corresponding to signal K of FIG. 38A), which will change as red blood cells are returned to the channel 86 via the high-G outlet passage 98b when harvesting the buffy coat. It is also within the scope of the present disclosure for the controller to analyze one interface radial position during one stage of a procedure and a different interface radial position during another stage of the same procedure.

As noted above, but emphasized again, it should be understood that, while certain features are shown in combination with other features, such chamber features may be employed independently of each other. Additionally, it should be understood that the features of the different embodiments described herein may be used in different combinations, such as the air drain taper 112 of the chamber 52a of FIGS. 14-16 be used in combination with the ramp 100a and inlet passage 88a of the chamber 52c of FIGS. 26 and 27. Thus, it should be clear that the embodiments described herein are merely exemplary and illustrative of possible implementations and combinations of different features that may be differently combined and/or employed independently in fluid separation chambers, rather than being limiting.

Aspects

Aspect 1. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end and a downstream end; and a plurality of radial walls extending from the central hub to the separation channel to define a terminal wall separating the upstream end of the separation channel from the downstream end of the separation channel, an inlet passage at the upstream end of the separation channel, and low-G and high-G outlet passages, wherein the low-G and high-G outlet passages open into the separation channel at a bottom end of the separation channel, a bottom end of the high-G wall has an at least substantially uniform radius from the upstream end of the separation channel to the downstream end of the separation channel, and a bottom end of the low-G wall includes an air drain taper having a width that increases from the upstream end of the separation channel to the downstream end of the separation channel so as to decrease the radius of the bottom end of the low-G wall from the upstream end of the separation channel to the downstream end of the separation channel and increase a width of the bottom end of the separation channel from the upstream end of the separation channel to the downstream end of the separation channel.

Aspect 2. The fluid separation chamber of Aspect 1, wherein the air drain taper has a radius configured as a uniform spiral.

Aspect 3. The fluid separation chamber of Aspect 1, wherein the air drain taper has a radius configured as a uniform spiral having a pitch of approximately 0.16 cm.

Aspect 4. The fluid separation chamber of any one of the preceding Aspects, wherein the air drain taper has a height in a range of approximately 0.15 cm to approximately 0.25 cm.

Aspect 5. The fluid separation chamber of any one of the preceding Aspects, wherein the air drain taper has a height of approximately 0.2 cm.

Aspect 6. The fluid separation chamber of any one of the preceding Aspects, wherein the air drain taper has a substantially uniform height.

Aspect 7. The fluid separation chamber of any one of the preceding Aspects, wherein the low-G and high-G outlet passages open into the separation channel at the downstream end of the separation channel.

Aspect 8. The fluid separation chamber of any one of the preceding Aspects, further comprising a ramp extending generally diagonally across the separation channel from the high-G wall at a first position to the low-G wall at a second position downstream of the first position, wherein the ramp is positioned at the downstream end of the separation channel.

Aspect 9. The fluid separation chamber of Aspect 8, wherein the low-G and high-G outlet passages open into the separation channel at the downstream end of the separation channel, a bottom end of the ramp is separated from the bottom end of the separation channel by a gap, a cell settling well defined between the bottom end of the ramp and the bottom end of the separation channel is configured to allow fluid flow through said gap, and a surface of the cell settling well is defined by a generally planar extension of the low-G wall, with the extension extending from a first end to a second end downstream of the first end, and with the low-G wall having a smaller radius at the second end than at the first end.

Aspect 10. The fluid separation chamber of Aspect 9, wherein the low-G outlet passage opens into the separation channel at the second end of said extension.

Aspect 11. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end and a downstream end; and a plurality of radial walls extending from the central hub to the separation channel to define a terminal wall separating the upstream end of the separation channel from the downstream end of the separation channel, an inlet passage at the upstream end of the separation channel, and low-G and high-G outlet passages, wherein the high-G wall has an at least substantially uniform radius from the upstream end of the separation channel to the downstream end of the separation channel at each axial position, and the low-G wall has a radius that decreases from the upstream end of the separation channel to the downstream end of the separation channel at each axial position so as to increase a width of the separation channel from the upstream end of the separation channel to the downstream end of the separation channel at each axial position.

Aspect 12. The fluid separation chamber of Aspect 11, wherein the low-G wall has a radius configured as a uniform spiral.

Aspect 13. The fluid separation chamber of any one of Aspects 11-12, wherein the low-G and high-G outlet passages open into the separation channel at the downstream end of the separation channel.

Aspect 14. The fluid separation chamber of any one of Aspects 11-13, further comprising a ramp extending generally diagonally across the separation channel from the high-G wall at a first position to the low-G wall at a second position downstream of the first position, wherein the ramp is positioned at the downstream end of the separation channel.

Aspect 15. The fluid separation chamber of Aspect 14, wherein the low-G and high-G outlet passages open into the separation channel at a bottom end of the downstream end of the separation channel, a first portion of the ramp extends to the bottom end of the separation channel, a second portion of the ramp has a bottom end separated from the bottom end of the separation channel by a gap, and a fluid velocity reduction feature defined between the bottom end of the second portion of the ramp and the bottom end of the separation channel is configured to allow fluid flow through said gap.

Aspect 16. The fluid separation chamber of Aspect 15, wherein the low-G outlet passage opens into the separation channel at a downstream end of the fluid velocity reduction feature.

Aspect 17. The fluid separation chamber of any one of Aspects 14-16, wherein the high-G outlet passage opens into the separation channel at the first position of the ramp.

Aspect 18. The fluid separation chamber of any one of Aspects 11-17, wherein the low-G wall includes a generally planar extension at the downstream end of the separation channel, a portion of the extension extends along an entire height of the separation channel, with the extension extending from a first end to a second end downstream of the first end, and with the low-G wall having a smaller radius at the second end than at the first end, and the low-G outlet passage opens into the separation channel at the second end of the extension.

Aspect 19. The fluid separation chamber of Aspect 18, further comprising a ramp at the downstream end of the separation channel, wherein the ramp extends generally diagonally across the separation channel from the high-G wall at a first position to the low-G wall at a second position downstream of the first position, and the second position of the ramp coincides with the second end of the extension.

Aspect 20. The fluid separation chamber of any one of Aspects 11-19, further comprising a ramp at the downstream end of the separation channel, wherein the ramp extends generally diagonally across the separation channel from the high-G wall at a first position to the low-G wall at a second position downstream of the first position, and a top end of the ramp is positioned substantially directly above a bottom end of the ramp.

Aspect 21. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end and a downstream end; a plurality of radial walls extending from the central hub to the separation channel to define a terminal wall separating the upstream end of the separation channel from the downstream end of the separation channel, an inlet passage at the upstream end of the separation channel, and low-G and high-G outlet passages opening into the separation channel at a bottom end of the separation channel; and a ramp extending generally diagonally across the separation channel from the high-G wall at a first position to the low-G wall at a second position downstream of the first position, with a portion of the ramp extending to the bottom end of the separation channel.

Aspect 22. The fluid separation chamber of Aspect 21, wherein the low-G and high-G outlet passages open into the separation channel at the downstream end of the separation channel.

Aspect 23. The fluid separation chamber of any one of Aspects 21-22, wherein the ramp is positioned at the downstream end of the separation channel.

Aspect 24. The fluid separation chamber of any one of Aspects 21-23, wherein a second portion of the ramp has a bottom end separated from the bottom end of the separation channel by a gap, and a fluid velocity reduction feature defined between the bottom end of the second portion of the ramp and the bottom end of the separation channel is configured to allow fluid flow through said gap.

Aspect 25. The fluid separation chamber of Aspect 24, wherein the low-G outlet passage opens into the separation channel at a downstream end of the fluid velocity reduction feature.

Aspect 26. The fluid separation chamber of any one of Aspects 21-25, wherein the high-G outlet passage opens into the separation channel at the first position of the ramp.

Aspect 27. The fluid separation chamber of any one of Aspects 21-26, wherein the low-G wall includes a generally planar extension at the downstream end of the separation channel, a portion of the extension extends along an entire height of the separation channel, with the extension extending from a first end to a second end downstream of the first end, and with the low-G wall having a smaller radius at the second end than at the first end, and the low-G outlet passage opens into the separation channel at the second end of the extension.

Aspect 28. The fluid separation chamber of Aspect 27, wherein the second position of the ramp coincides with the second end of the extension.

Aspect 29. The fluid separation chamber of any one of Aspects 21-28, wherein the inlet passage opens into the separation channel at a top end of the separation channel.

Aspect 30. The fluid separation chamber of any one of Aspects 21-29, wherein a top end of the ramp is positioned substantially directly above a bottom end of the ramp.

Aspect 31. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end and a downstream end; and a plurality of radial walls extending from the central hub to the separation channel to define a terminal wall separating the upstream end of the separation channel from the downstream end of the separation channel, an inlet passage at the upstream end of the separation channel, and low-G and high-G outlet passages, wherein the low-G wall includes a generally planar extension at the downstream end of the separation channel, a portion of the extension extends along an entire height of the separation channel, with the extension extending from a first end to a second end downstream of the first end; and with the low-G wall having a smaller radius at the second end than at the first end, and the low-G outlet passage opens into the separation channel at the second end of the extension.

Aspect 32. The fluid separation chamber of Aspect 31, wherein the high-G outlet passage opens into the separation channel at the downstream end of the separation channel.

Aspect 33. The fluid separation chamber of any one of Aspects 31-32, wherein the low-G and high-G outlet passages open into the separation channel at a bottom end of the separation channel.

Aspect 34. The fluid separation chamber of any one of Aspects 31-33, further comprising a ramp at the downstream end of the separation channel, wherein the ramp extends generally diagonally across the separation channel from the high-G wall at a first position to the low-G wall at a second position downstream of the first position, and the second position of the ramp coincides with the second end of the extension.

Aspect 35. The fluid separation chamber of Aspect 34, wherein a portion of the ramp extends to the bottom end of the separation channel.

Aspect 36. The fluid separation chamber of any one of Aspects 34-35, wherein at least a portion of the extension is angularly aligned with the ramp.

Aspect 37. The fluid separation chamber of any one of Aspects 34-36, wherein a top end of the ramp is positioned substantially directly above a bottom end of the ramp.

Aspect 38. The fluid separation chamber of any one of Aspects 35-37, wherein a second portion of the ramp has a bottom end separated from a bottom end of the separation channel by a gap, and a fluid velocity reduction feature defined between the bottom end of the second portion of the ramp and the bottom end of the separation channel is configured to allow fluid flow through said gap.

Aspect 39. The fluid separation chamber of Aspect 38, wherein the low-G outlet passage opens into the separation channel at a downstream end of the fluid velocity reduction feature.

Aspect 40. The fluid separation chamber of any one of Aspects 34-39, wherein the high-G outlet passage opens into the separation channel at the first position of the ramp.

Aspect 41. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end and a downstream end; a plurality of radial walls extending from the central hub to the separation channel to define a terminal wall separating the upstream end of the separation channel from the downstream end of the separation channel, an inlet passage at the upstream end of the separation channel, and low-G and high-G outlet passages; and a ramp extending generally diagonally across the separation channel from the high-G wall at a first position to the low-G wall at a second position downstream of the first position, wherein the ramp is positioned at the downstream end of the separation channel.

Aspect 42. The fluid separation chamber of Aspect 41, wherein the low-G and high-G outlet passages open into the separation channel at the downstream end of the separation channel.

Aspect 43. The fluid separation chamber of any one of Aspects 41-42, wherein the low-G and high-G outlet passages open into the separation channel downstream of the ramp.

Aspect 44. The fluid separation chamber of Aspect 43, wherein a bottom end of the ramp is separated from a bottom end of the separation channel by a gap, a cell settling well defined between the bottom end of the ramp and the bottom end of the separation channel is configured to allow fluid flow through said gap, and a surface of the cell settling well is defined by a generally planar extension of the low-G wall, with the extension extending from a first end to a second end downstream of the first end, and with the low-G wall having a smaller radius at the second end than at the first end.

Aspect 45. The fluid separation chamber of any one of Aspects 41-42, wherein the low-G outlet passage opens into the separation channel downstream of the ramp, and the high-G outlet passage opens into the separation channel at the first position of the ramp.

Aspect 46. The fluid separation chamber of Aspect 45, wherein the low-G and high-G outlet passages open into the separation channel at a bottom end of the separation channel, and a portion of the ramp extends to the bottom end of the separation channel.

Aspect 47. The fluid separation chamber of Aspect 46, wherein a second portion of the ramp has a bottom end separated from the bottom end of the separation channel by a gap, and a fluid velocity reduction feature defined between the bottom end of the second portion of the ramp and the bottom end of the separation channel is configured to allow fluid flow through said gap.

Aspect 48. The fluid separation chamber of any one of Aspects 45-47, where the low-G wall includes a generally planar extension at the downstream end of the separation channel, a portion of the extension extends along an entire height of the separation channel, with the extension extending from a first end to a second end downstream of the first end, and with the low-G wall having a smaller radius at the second end than at the first end, and the low-G outlet passage opens into the separation channel at the second end of the extension.

Aspect 49. The fluid separation chamber of Aspect 48, wherein the second position of the ramp coincides with the second end of the extension.

Aspect 50. The fluid separation chamber of any one of Aspects 45-49, wherein a top end of the ramp is positioned substantially directly above a bottom end of the ramp.

Aspect 51. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end and a downstream end; a plurality of radial walls extending from the central hub to the separation channel to define a terminal wall separating the upstream end of the separation channel from the downstream end of the separation channel, an inlet passage at the upstream end of the separation channel, and low-G and high-G outlet passages; and a ramp extending generally diagonally across the separation channel from the high-G wall at a first position to the low-G wall at a second position downstream of the first position, wherein the high-G outlet passage opens into the separation channel at the first position of the ramp.

Aspect 52. The fluid separation chamber of Aspect 51, wherein the low-G and high-G outlet passages open into the separation channel at the downstream end of the separation channel, and the ramp is positioned at the downstream end of the separation channel.

Aspect 53. The fluid separation chamber of any one of Aspects 51-52, wherein the low-G outlet passage opens into the separation channel at the second position of the ramp.

Aspect 54. The fluid separation chamber of any one of Aspects 51-53, wherein the low-G and high-G outlet passages open into the separation channel at a bottom end of the separation channel.

Aspect 55. The fluid separation chamber of Aspect 54, wherein a portion of the ramp extends to the bottom end of the separation channel.

Aspect 56. The fluid separation chamber of Aspect 46, wherein a second portion of the ramp has a bottom end separated from the bottom end of the separation channel by a gap, and a fluid velocity reduction feature defined between the bottom end of the second portion of the ramp and the bottom end of the separation channel is configured to allow fluid flow through said gap.

Aspect 57. The fluid separation chamber of any one of Aspects 51-56, where the low-G wall includes a generally planar extension at the downstream end of the separation channel, a portion of the extension extends along an entire height of the separation channel, with the extension extending from a first end to a second end downstream of the first end, and with the low-G wall having a smaller radius at the second end than at the first end, and the low-G outlet passage opens into the separation channel at the second end of the extension.

Aspect 58. The fluid separation chamber of Aspect 57, wherein the second position of the ramp coincides with the second end of the extension.

Aspect 59. The fluid separation chamber of any one of Aspects 57-58, wherein at least a portion of the extension is angularly aligned with the ramp.

Aspect 60. The fluid separation chamber of any one of Aspects 51-59, wherein a top end of the ramp is positioned substantially directly above a bottom end of the ramp.

Aspect 61. A fluid separation chamber for rotation about an axis, comprising: a central hub coinciding with the axis; a generally annular low-G wall and a generally annular high-G wall extending about the central hub in a spaced apart relationship to define therebetween a single-stage separation channel having an upstream end and a downstream end; and a plurality of radial walls extending from the central hub to the separation channel to define a terminal wall separating the upstream end of the separation channel from the downstream end of the separation channel, an inlet passage at the upstream end of the separation channel, and low-G and high-G outlet passages, wherein the high-G wall has a radius that decreases from the upstream end of the separation channel to the downstream end of the separation channel at each axial position, the low-G wall has a radius that decreases from the upstream end of the separation channel to the downstream end of the separation channel at each axial position, and a width of the separation channel is at least substantially uniform from the upstream end of the separation channel to the downstream end of the separation channel at each axial position.

Aspect 62. The fluid separation chamber of Aspect 61, wherein each of the low-G wall and the high-G wall has a radius configured as a uniform spiral at each axial position.

Aspect 63. The fluid separation chamber of any one of Aspects 61-62, wherein the low-G outlet passage opens into the separation channel at the downstream end of the separation channel and the high-G outlet passage opens into the separation channel at the upstream end of the separation channel.

Aspect 64. The fluid separation chamber of Aspect 63, wherein the inlet passage opens into the separation channel at a top end of the separation channel and the high-G outlet passage opens into the separation channel at a bottom end of the separation channel.

Aspect 65. The fluid separation chamber of any one of Aspects 61-64, further comprising a ramp extending generally diagonally across the separation channel from the high-G wall at a first position to the low-G wall at a second position downstream of the first position, wherein the ramp is positioned at the downstream end of the separation channel.

Aspect 66. The fluid separation chamber of Aspect 65, wherein the low-G outlet passage opens into the separation channel at the second position of the ramp.

Aspect 67. The fluid separation chamber of any one of Aspects 65-66, wherein a bottom end of the ramp is separated from a bottom end of the separation channel by a gap, and a cell sewing well defined between the bottom end of the ramp and the bottom end of the separation channel is configured to allow fluid flow through said gap.

Aspect 68. The fluid separation chamber of Aspect 67, wherein the low-G outlet passage opens into the separation channel at a downstream end of the cell settling well.

Aspect 69. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end, a downstream end, a top end, and a bottom end; and a plurality of radial walls extending from the central hub to the separation channel to define a terminal wall separating the upstream end of the separation channel from the downstream end of the separation channel, an inlet passage at the upstream end of the separation channel, and low-G and high-G outlet passages, wherein the inlet passage opens into the separation channel at the top end of the separation channel, and the high-G outlet passage opens into the separation channel at the bottom end of the separation channel, at the upstream end of the separation channel.

Aspect 70. The fluid separation chamber of Aspect 69, wherein the low-G outlet passage opens into the separation channel at the downstream end of the separation channel.

Aspect 71. The fluid separation chamber of any one of Aspects 69-70, wherein the high-G wall has a radius that decreases from the upstream end of the separation channel to the downstream end of the separation channel at each axial position.

Aspect 72. The fluid separation chamber of any one of Aspects 69-71, wherein the low-G wall has a radius that decreases from the upstream end of the separation channel to the downstream end of the separation channel at each axial position.

Aspect 73. The fluid separation chamber of any one of Aspects 69-70, wherein the high-G wall has a radius that decreases from the upstream end of the separation channel to the downstream end of the separation channel at each axial position, and the low-G wall has a radius that decreases from the upstream end of the separation channel to the downstream end of the separation channel at each axial position.

Aspect 74. The fluid separation chamber of Aspect 73, wherein a width of the separation channel is at least substantially uniform from the upstream end of the separation channel to the downstream end of the separation channel at each axial position.

Aspect 75. The fluid separation chamber of any one of Aspects 73-74, wherein each of the low-G wall and the high-G wall has a radius configured as a uniform spiral at each axial position.

Aspect 76. The fluid separation chamber of any one of Aspects 69-75, further comprising a ramp extending generally diagonally across the separation channel from the high-G wall at a first position to the low-G wall at a second position downstream of the first position, wherein the ramp is positioned at the downstream end of the separation channel.

Aspect 77. The fluid separation chamber of Aspect 76, wherein the low-G outlet passage opens into the separation channel at the second position of the ramp.

Aspect 78. The fluid separation chamber of any one of Aspects 76-77, wherein a bottom end of the ramp is separated from the bottom end of the separation channel by a gap, and a cell settling well defined between the bottom end of the ramp and the bottom end of the separation channel is configured to allow fluid flow through said gap.

Aspect 79. The fluid separation chamber of Aspect 78, wherein the low-G outlet passage opens into the separation channel at a downstream end of the cell settling well.

Aspect 80. A fluid separation chamber for rotation about an axis, comprising: a central hub coinciding with the axis; a generally annular low-G wall and a generally annular high-G wall extending about the central hub in a spaced apart relationship to define therebetween a single-stage separation channel having an upstream end and a downstream end; and a plurality of radial walls extending from the central hub to the separation channel to define a terminal wall separating the upstream end of the separation channel from the downstream end of the separation channel, an inlet passage at the upstream end of the separation channel, and low-G and high-G outlet passages, wherein the inlet passage opens into the separation channel at the top end of the separation channel, the high-G outlet passage opens into the separation channel at the bottom end of the separation channel, at the upstream end of the separation channel, the high-G wall has a radius that decreases from the upstream end of the separation channel to the downstream end of the separation channel at each axial position, the low-G wall has a radius that decreases from the upstream end of the separation channel to the downstream end of the separation channel at each axial position, and a width of the separation channel is at least substantially uniform from the upstream end of the separation channel to the downstream end of the separation channel at each axial position.

Aspect 81. The fluid separation chamber of Aspect 80, wherein each of the low-G wall and the high-G wall has a radius configured as a uniform spiral at each axial position.

Aspect 82. The fluid separation chamber of any one of Aspects 80-81, wherein the low-G outlet passage opens into the separation channel at the downstream end of the separation channel.

Aspect 83. The fluid separation chamber of any one of Aspects 80-82, further comprising a ramp extending generally diagonally across the separation channel from the high-G wall at a first position to the low-G wall at a second position downstream of the first position, wherein the ramp is positioned at the downstream end of the separation channel.

Aspect 84. The fluid separation chamber of Aspect 83, wherein the low-G outlet passage opens into the separation channel at the second position of the ramp.

Aspect 85. The fluid separation chamber of any one of Aspects 83-84, wherein a bottom end of the ramp is separated from the bottom end of the separation channel by a gap, and a cell settling well defined between the bottom end of the ramp and the bottom end of the separation channel is configured to allow fluid flow through said gap.

Aspect 86. The fluid separation chamber of Aspect 85, wherein the low-G outlet passage opens into the separation channel at a downstream end of the cell settling well.

Aspect 87. A fluid separation chamber for rotation about an axis, comprising: a central hub coinciding with the axis; a generally annular low-G wall and a generally annular high-G wall extending about the central hub in a spaced apart relationship to define therebetween a separation channel having an upstream end and a downstream end; a plurality of radial walls extending from the central hub to the separation channel to define a terminal wall separating the upstream end of the separation channel from the downstream end of the separation channel, an inlet passage at the upstream end of the separation channel, and low-G and high-G outlet passages; and first and second ramps each extending generally diagonally across the separation channel, wherein the first ramp is positioned at the downstream end of the separation channel and the second ramp is positioned at the upstream end of the separation channel.

Aspect 88. The fluid separation chamber of Aspect 87, wherein the first ramp extends from the high-G wall to the low-G wall at a downstream position.

Aspect 89. The fluid separation chamber of any one of Aspects 87-88, wherein the second ramp extends from the low-G wall to the high-G wall at a downstream position.

Aspect 90. The fluid separation chamber of any one of Aspects 87-89, wherein the second ramp has a greater length than the first ramp.

Aspect 91. The fluid separation chamber of any one of Aspects 87-90, wherein the first ramp extends across the separation channel at a first angle, the second ramp extends across the separation channel at a second angle, and the second angle is different from the first angle.

Aspect 92. The fluid separation chamber of any one of Aspects 87-90, wherein the first ramp extends across the separation channel at a first angle, the second ramp extends across the separation channel at a second angle, and the second angle is equal to the first angle.

Aspect 93. The fluid separation chamber of any one of Aspects 87-92, wherein the low-G outlet passage opens into the separation channel at the downstream end of the separation channel.

Aspect 94. The fluid separation chamber of any one of Aspects 87-93, wherein the high-G outlet passage opens into the separation channel at the upstream end of the separation channel.

Aspect 95. The fluid separation chamber of any one of Aspects 87-94, wherein the high-G outlet passage opens into the separation channel at an upstream end of the second ramp, and the low-G outlet passage opens into the separation channel at a downstream end of the first ramp.

Aspect 96. The fluid separation chamber of any one of Aspects 87-95, wherein the inlet passage opens into the separation channel at a top end of the separation channel, and the low-G and high-G outlet passages open into the separation channel at a bottom end of the separation channel.

Aspect 97. A method of determining a radial position of an interface between separated fluid components within a separation channel of a fluid separation chamber, comprising: optically detecting a first radial position of the interface between separated fluid components within the separation channel at a downstream end of the separation channel; optically detecting a second radial position of the interface between separated fluid components within the separation channel at an upstream end of the separation channel; and determining the radial position of the interface based on at least one of the first and second radial positions.

Aspect 98. The method of Aspect 97, wherein said determining the radial position of the interface based on at least one of the first and second radial positions comprises equating the radial position of the interface to the first radial position.

Aspect 99. The method of Aspect 97, wherein said determining the radial position of the interface based on at least one of the first and second radial positions comprises equating the radial position of the interface to the second radial position.

Aspect 100. The method of Aspect 97, wherein said determining the radial position of the interface based on at least one of the first and second radial positions comprises equating the radial position of the interface to neither the first radial position nor the second radial position.

Aspect 101. The method of Aspect 97, wherein said determining the radial position of the interface based on at least one of the first and second radial positions comprises equating the radial position of the interface to an average of the first and second radial positions.

Aspect 102. An interface monitoring system for determining a radial position of an interface between separated fluid components within a separation channel of a fluid separation chamber, comprising: a light source configured to transmit a light into the fluid separation chamber and through the separation channel at downstream and upstream ends of the separation channel; a light detector configured to receive at least a portion of the light transmitted through the downstream end of the separation channel and generate a first signal indicative of a first radial position of the interface at the downstream end of the separation channel and to receive at least a portion of the light transmitted through the upstream end of the separation channel and generate a second signal indicative of a second radial position of the interface at the upstream end of the separation channel; and a controller configured to receive said first and second signals and determine the radial position of the interface based on at least one of the first and second signals.

Aspect 103. The interface monitoring system of Aspect 102, wherein the controller is configured to determine the radial position of the interface by equating the radial position of the interface to the first radial position.

Aspect 104. The interface monitoring system of Aspect 102, wherein the controller is configured to determine the radial position of the interface by equating the radial position of the interface to the second radial position.

Aspect 105. The interface monitoring system of Aspect 102, wherein the controller is configured to determine the radial position of the interface by equating the radial position of the interface to neither the first radial position nor the second radial position.

Aspect 106. The interface monitoring system of Aspect 102, wherein the controller is configured to determine the radial position of the interface by equating the radial position of the interface to an average of the first and second radial positions.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A combination of a single-stage centrifuge and a single-stage fluid separation chamber configured to be received within the single-stage centrifuge for rotation about an axis, wherein the single-stage fluid separation chamber includes
   a central hub coinciding with the axis;
   a generally annular low-G wall and a generally annular high-G wall extending about the central hub in a spaced apart relationship to define therebetween a single-stage separation channel having an upstream end and a downstream end; and
   a plurality of radial walls extending from the central hub to the single-stage separation channel to define a terminal wall separating the upstream end of the single-stage separation channel from the downstream end of the single-stage separation channel, an inlet passage at the upstream end of the single-stage separation channel, and low-G and high-G outlet passages, wherein
      the high-G wall has a radius that decreases from the upstream end of the single-stage separation channel to the downstream end of the single-stage separation channel at each axial position,
      the low-G wall has a radius that decreases from the upstream end of the single-stage separation channel to the downstream end of the single-stage separation channel at each axial position, and
      a width of the single-stage separation channel is at least substantially uniform from the upstream end of the single-stage separation channel to the downstream end of the single-stage separation channel at each axial position.

2. The combination of claim 1, wherein each of the low-G wall and the high-G wall has a radius configured as a uniform spiral at each axial position.

3. The combination of claim 1, wherein the low-G outlet passage opens into the single-stage separation channel at the downstream end of the single-stage separation channel and the high-G outlet passage opens into the single-stage separation channel at the upstream end of the single-stage separation channel.

4. The combination of claim 3, wherein the inlet passage opens into the single-stage separation channel at a top end of the single-stage separation channel and the high-G outlet passage opens into the single-stage separation channel at a bottom end of the single-stage separation channel.

5. The combination of claim 1, further comprising a ramp extending generally diagonally across the single-stage separation channel from the high-G wall at a first position to the low-G wall at a second position downstream of the first position, wherein the ramp is positioned at the downstream end of the single-stage separation channel.

6. The combination of claim 5, wherein the low-G outlet passage opens into the single-stage separation channel at the second position of the ramp.

7. The combination of claim 5, wherein
a bottom end of the ramp is separated from a bottom end of the single-stage separation channel by a gap, and
a cell settling well defined between the bottom end of the ramp and the bottom end of the single-stage separation channel is configured to allow fluid flow through said gap.

8. The combination of claim 7, wherein the low-G outlet passage opens into the single-stage separation channel at a downstream end of the cell settling well.

9. A combination of a single-stage centrifuge and a single-stage fluid separation chamber configured to be received within the single-stage centrifuge for rotation about an axis, wherein the single-stage fluid separation chamber includes
a central hub coinciding with the axis;
a generally annular low-G wall and a generally annular high-G wall extending about the central hub in a spaced apart relationship to define therebetween a single-stage separation channel having an upstream end, a downstream end, a top end, and a bottom end; and
a plurality of radial walls extending from the central hub to the single-stage separation channel to define a terminal wall separating the upstream end of the single-stage separation channel from the downstream end of the single-stage separation channel, an inlet passage at the upstream end of the single-stage separation channel, and low-G and high-G outlet passages, wherein
the inlet passage opens into the single-stage separation channel at the top end of the single-stage separation channel, and
the high-G outlet passage opens into the single-stage separation channel at the bottom end of the single-stage separation channel, at the upstream end of the single-stage separation channel.

10. The combination of claim 9, wherein the low-G outlet passage opens into the single-stage separation channel at the downstream end of the single-stage separation channel.

11. The combination of claim 9, wherein the high-G wall has a radius that decreases from the upstream end of the single-stage separation channel to the downstream end of the single-stage separation channel at each axial position.

12. The combination of claim 9, wherein the low-G wall has a radius that decreases from the upstream end of the single-stage separation channel to the downstream end of the single-stage separation channel at each axial position.

13. The combination of claim 9, wherein
the high-G wall has a radius that decreases from the upstream end of the single-stage separation channel to the downstream end of the single-stage separation channel at each axial position, and
the low-G wall has a radius that decreases from the upstream end of the single-stage separation channel to the downstream end of the single-stage separation channel at each axial position.

14. The combination of claim 13, wherein a width of the single-stage separation channel is at least substantially uniform from the upstream end of the single-stage separation channel to the downstream end of the single-stage separation channel at each axial position.

15. The combination of claim 13, wherein each of the low-G wall and the high-G wall has a radius configured as a uniform spiral at each axial position.

16. The combination of claim 9, further comprising a ramp extending generally diagonally across the single-stage separation channel from the high-G wall at a first position to the low-G wall at a second position downstream of the first position, wherein the ramp is positioned at the downstream end of the single-stage separation channel.

17. The combination of claim 16, wherein the low-G outlet passage opens into the single-stage separation channel at the second position of the ramp.

18. The combination of claim 16, wherein
a bottom end of the ramp is separated from the bottom end of the single-stage separation channel by a gap, and
a cell settling well defined between the bottom end of the ramp and the bottom end of the single-stage separation channel is configured to allow fluid flow through said gap.

19. The combination of claim 18, wherein the low-G outlet passage opens into the single-stage separation channel at a downstream end of the cell settling well.

20. A combination of a single-stage centrifuge and a single-stage fluid separation chamber configured to be received within the single-stage centrifuge for rotation about an axis, wherein the single-stage fluid separation chamber includes
a central hub coinciding with the axis;
a generally annular low-G wall and a generally annular high-G wall extending about the central hub in a spaced apart relationship to define therebetween a single-stage separation channel having an upstream end and a downstream end; and
a plurality of radial walls extending from the central hub to the single-stage separation channel to define a terminal wall separating the upstream end of the single-stage separation channel from the downstream end of the single-stage separation channel, an inlet passage at the upstream end of the single-stage separation channel, and low-G and high-G outlet passages, wherein
the inlet passage opens into the single-stage separation channel at the top end of the single-stage separation channel,
the high-G outlet passage opens into the single-stage separation channel at the bottom end of the single-stage separation channel, at the upstream end of the single-stage separation channel,
the high-G wall has a radius that decreases from the upstream end of the single-stage separation channel to the downstream end of the single-stage separation channel at each axial position,
the low-G wall has a radius that decreases from the upstream end of the single-stage separation channel to the downstream end of the single-stage separation channel at each axial position, and a width of the single-stage separation channel is at least substantially uniform from the upstream end of the single-stage separation channel to the downstream end of the single-stage separation channel at each axial position.

* * * * *